US006297401B1

(12) United States Patent
Miesel et al.

(10) Patent No.: US 6,297,401 B1
(45) Date of Patent: Oct. 2, 2001

(54) FUNGICIDAL COMPOSITIONS AND METHODS, AND COMPOUNDS AND METHODS FOR THE PREPARATION THEREOF

(75) Inventors: John L. Miesel; Zoltan L. Benko; William H. Dent, III; Gregory L. Durst, all of Indianapolis; Gina M. Fitzpatrick, Westfield; David D. Johnson, Greenfield; Sylvester V. Kaster, Indianapolis; Gregory M. Kemmitt, Lafayette; William C. Lo, Indianapolis, all of IN (US); Marc J. McKennon, Issaquah, WA (US); Ann B. Orth, Langhorne, PA (US); Michael J. Ricks, Indianapolis, IN (US); Richard B. Rogers, Zionsville, IN (US); Todd L. Werk, Indianapolis, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

(21) Appl. No.: 09/205,266

(22) Filed: Dec. 4, 1998

Related U.S. Application Data

(60) Provisional application No. 60/067,463, filed on Dec. 4, 1997.

(51) Int. Cl.$^7$ .......................... C07C 233/74; A01N 37/44

(52) U.S. Cl. ........................................... 564/166; 514/563

(58) Field of Search ............................. 564/166; 514/563

(56) References Cited

U.S. PATENT DOCUMENTS

| | | | |
|---|---|---|---|
| 3,459,534 | * | 8/1969 | Dorfman ................ 71/118 |
| 3,994,975 | * | 11/1976 | Oude Alink et al. ........... 260/563 |
| 5,034,393 | * | 7/1991 | Hackler et al. ............... 514/258 |
| 5,292,743 | * | 3/1994 | Liebeschuetz ............... 514/275 |
| 5,447,960 | * | 9/1995 | Sinnott et al. ............... 514/732 |

FOREIGN PATENT DOCUMENTS

| | | | |
|---|---|---|---|
| 4110483A1 | * | 10/1992 | (DE) . |
| 1-228949 | * | 9/1989 | (JP) . |
| 3-95141 | * | 4/1991 | (JP) . |
| WO 97/08135 | * | 3/1997 | (WO) . |

OTHER PUBLICATIONS

Hutchins et al., "Stereoselective Reductions of Substituted Cyclohexyl and Cyclopentyl Carbon–Nitrogen π Systems with Hydride Reagents", *J. Org. Chem*, 1983, 48, 3412–3422.

Selwood et al., Structure–Activity Relationships of Antifilarial Antimycin Analogues: A Multivariate Pattern Recognition Study, *J. Med. Chem.*, 1990, 33, 136–142.

Neft et al., Inhibition of Electron Transport by Substituted Salicyl–N–(n–octadecyl)amides, Department of Chemistry, Utah State University, *Chem. Abstr.* 76, 94491e, *J. Med. Chem.* 14, 1169 (1971).

Dickie et al., The Chemistry of Antimycin A. XI. N–Substituted 3–Formamidosalicylic Amides, *J Med. Chem.*, vol. 6, Jul. 1963, pp. 424–427.

Tokutake et al., Structural Factors of Antmycin A Molecule Required for Inhibitory Action, *Biochimica et Biophysica Acta*, 1185 (1994) 271–278.

Aburaki et al., Synthesis of Deisovalerylblastmycin, *Chemistry Letters*, pp. 701–704 (1976), published by Chemical Society of Japan.

Kinoshita et al., Syntheses of (3S, 4R, 15S)–4,15–Dimethyl–1, 5–dioxa–3–(3'–formamidolsalicylamido)–cyclopentadecane–2,6–dione and its (15R)–Epimer, New Antimycin Analogs, *Bulletin of the Chemical Society of Japan*, vol. 44, No. 12, (1971).

Taborsky et al., Substituted Salicylanilides III, *J. Pharm. Sci.*, vol. 52, No. 6, (1963) pp. 542–545.

Abidi et al., Liquid chromatography–thermospray mass spectrometric study of N–acylamino dilactones and 4–butyrolactones derived from antimycin A, *J. of Chromatography*, 522 (1990) 179–194.

Miyoshi et al., A model of antimycin A binding based on structure–activity studies of synthetic anitmycin A analogues, *Biochim. et Biophysica Acta* 1229 (1995) 149–154.

Xu et al., Comparison between the properties of 3–nitrosalicyl–N–alkylamide and antimycin A acting on $QH_2$: cytochrome c reductase, *Biochim. et Biophysica Acta,*, 1142 (1993) 83–87.

Communication to the Editor, Journal of Antibiotics vol. 46, No. 4, (1992), pp. 701–703.

Caglioti et al., The Structure of Neoantimycin, *Tetrahedron*, vol. 25, pp. 2193–2221 (1969).

Immamura et al., Novel Antimycin Antibiotics, Urauchimycins A and B, Produced by Marine Actinomycete, J. of Antibiotics, vol. 46, No. 2 (1992).

Tokutake et al., Inhibition of electron transport of rat–liver mitochondria by synthesized antimycin A analogs, Biochemica et Biophysica Acta, 1142 (1993) 262–268.

Keizo et al., Antimycin derivatives, *Chem. Abstracts* vol. 70, 1969, p. 310.

Makoto et al., Fungicides manufacture with streptoverticillium, *CA Selects: Fungicides*, Issue 26 (1995), p. 9.

Unknown number, Thionosalicylic Acid Anilides, Salts Thereof, Intermediates Therefor and Productions Processes, F. Bayer Akt., Kurz et al., South African patent application, dated Apr. 19, 1967.

* cited by examiner

Primary Examiner—Floyd D. Higel
Assistant Examiner—Ebenezer Sackey
(74) Attorney, Agent, or Firm—Carl D. Corvin; Donald R. Stuart; Thomas Q. Henry

(57) ABSTRACT

Fungicidal compositions and methods comprising acylated aminosalicylamides (AASA) described herein. Novel cyclic amines and 3-nitrosalicylamides, and their use as pesticides and in the preparation of the antifungal AASA compounds are also disclosed.

1 Claim, No Drawings

FUNGICIDAL COMPOSITIONS AND METHODS, AND COMPOUNDS AND METHODS FOR THE PREPARATION THEREOF

CROSS-REFERENCE TO RELATED APPLICATION

This application claims priority from U.S. Provisional Patent Application Serial No. 60/067,463 filed Dec. 4, 1997.

BACKGROUND OF THE INVENTION

1. Field of the Invention

The present invention relates to the field of fungicidal compositions and methods, and more particularly to plant fungicides and methods involving the application of fungicidally effective amounts of such compounds to the locus of a plant pathogen. The present invention also provides novel compounds and methods useful in the preparation of fimgicides, and fungicidal compositions.

2. Description of the Prior Art

A variety of antifungal compositions and methods are well known in the art. Antimycin, for example, has been identified as a naturally occurring substance produced by Streptomyces spp which has efficacy as a fungicide. However, there has remained a need for new fungicides. The present invention provides fungicides which have a high residual activity, greater activity at lower application rates, curative activity, and a broader spectrum of efficacy.

SUMMARY OF THE INVENTION

Briefly describing one aspect of the present invention, there are provided fungicidal compounds comprising acylated aminosalicylamides of the Formula I:

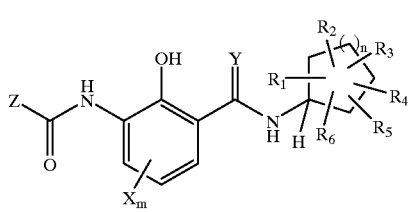

Formula I wherein m, n, X, Y, Z and $R_1$–$R_6$ are as hereafter defined. The invention also encompasses hydrates, salts and complexes thereof.

The present invention also provides fungicidal compositions comprising the acylated aminosalicylamides in combination with phytologically acceptable carriers and/or diluents. Methods for the use of the acylated aminosalicylamide compounds and compositions are also disclosed.

In another aspect, the present invention includes compounds and methods for preparation of the acylated aminosalicylamides. Encompassed are certain novel cyclic anmines and 3-nitrosalicylamides, including ones having fungicidal efficacy, as well as methods for the preparation thereof Also included are certain nitro intermediates and their method of preparation.

It is an object of the present invention to provide acylated aminosalicylamides and compositions thereof which are effective as antifungal agents.

Another object of the present invention is to provide methods for the control and/or prevention of fungus infestations, which methods include the application of acylated aminosalicylamides and compositions containing same.

The present invention also has an object the provision of certain cyclic amines, their method of preparation and use in producing acylated aminosalicylamides, and optionally the use of such amines as fungicides.

It is a further object of the present invention to provide certain 3-nitrosalicylamides useful as fimgicides and in the preparation of the fungicidal acylated aminosalicylamides.

Further objects and advantages of the present invention will be apparent from the description which follows.

DESCRIPTION OF THE PREFERRED EMBODIMENT

For the purposes of promoting an understanding of the principles of the invention, reference will now be made to the embodiments illustrated herein and specific language will be used to describe the same. It will nevertheless be understood that alterations, modifications and further applications of the invention are contemplated as would normally occur to one skilled in the art to which the invention relates. The present invention particularly contemplates such compounds, compositions and methods which are substantially equivalent to the inventions claimed herein.

General Scope of the Invention

The present invention relates to various acylated aminosalicylamide ("AASA") compounds which are active as antifungal agents. Also included are formulations including the acylated aminosalicylamide compounds, and methods of using the AASA compounds and formulations. The methods of preparing the AASA compounds are also encompassed by the present invention, as well as certain intermediate compounds, and their method of preparation and optional use as fungicides.

Acylated Aminosalicylamide Compounds

The novel antifungal AASA compounds of the present invention are described by the following Formula I:

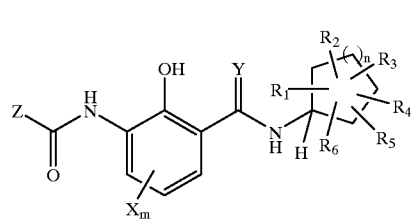

Formula I wherein:

a. m is 1 or 2;

b. ( )n represents n additional carbon atoms in the alicyclic ring, where n is 1, 2, 3 or 4;

c. X is hydrogen ("H"), halogen, $C_1$–$C_4$ alkyl, $C_2$–$C_4$ alkenyl, cyclopropyl, cyano, $NO_2$, $C_1$–$C_4$ haloalkyl, hydroxy, $C_1$–$C_3$ alkoxy, $C_1$–$C_3$ haloalkoxy, $C_1$–$C_3$ alKylthio, $C_1$–$C_3$ alkylsulfonyl, $C_1$–$C_3$ alkylsulfinyl, $C_1$–$C_2$ SCOalkyl, $C_1$–$C_3$ NHalkyl, $C_1$–$C_3$ N(alkyl)$_2$, $C_1$–$C_3$ NHCOalkyl, NHC(O)H, $C_1$–$C_3$N-alkyl COalkyl, $C_1$–$C_3$ NHCONHalkyl or $C_1$–$C_2$NHCON (alkyl)$_2$, C(O)$R_x$, C(O)O$R_x$, or C(O)N$R_x$,$R_x$, in which $R_x$, is H or $C_1$–$C_4$ alkyl;

d. Y is O, S, NOH, NH or $NOC_{1-3}$alkyl;

e. Z is H, $C_1$–$C_2$ alkyl, $CH_3NH$, $NH_2$ or $Me_2N$; and f. $R_1$–$R_6$ are defined as follows:

(i) each of $R_1$–$R_6$ is independently selected from the group consisting of:

1. H, halogen and cyano,
2. $C_1$–$C_8$ alkyl (straight chain or branched), $C_2$–$C_8$ alkenyl (straight chain or branched), $C_2$–$C_8$ alkynyl (straight chain or branched), $C_3$–$C_8$ cycloalkyl and $C_4$–$C_8$ cycloalkenyl, each of the foregoing groups being optionally substituted with one or more of: $OR_7$, $SR_7$, $SOR_{7a}$, $SO_2R_{7a}$, $NR_8R_{8a}$, halogen, cyano, cycloalkyl ($C_3$–$C_8$), $Si(C_1$–$C_4$ alkyl$)_3$, $C(O)OR_{7a}$, aryl or heterocycle,
3. $C_1$–$C_8$ alkoxycarbonyl (straight chain or branched), aryloxycarbonyl, $C_1$–$C_7$ (alkylthio) arbonyl (straight chain or branched), (arylthio) carbonyl, $C_1$–$C_7$ CONHalkyl, CONHaryl, $C_1$–$C_3$ CONalkylaryl, $C_1$–$C_4$ CONalkyl$_2$, or $COR_{11}$,
4. aryl or heterocycle, which may be the same or different, with the provision that no more than two of $R_1$–$R_6$ may be aryl or heterocycle,
5. $C_1$–$C_8$ alkoxy (straight-chain or branched), $C_3$–$C_8$ alkenyloxy, $C_3$–$C_8$ alkynyloxy, $C_3$–$C_8$ cycloalkoxy, $C_1$–$C_8$ haloalkoxy (straight chain or branched), $C_3$–$C_8$ alkoxyalkoxy, $C_3$–$C_8$ alkyl thioalkoxy, $C_1$–$C_8$ alkylthio (straight chain or branched), $C_3$–$C_8$ alkenylthio, $C_3$–$C_8$ alkynylthio, $C_3$–$C_8$ cycloalkylthio, $C_1$–$C_8$ haloalkylthio, $C_3$–$C_8$ alkoxyalkylthio, $OR_9$, $SR_9$, $NR_9R_{10}$, aryloxy, heterocycloxy, arylthio or heterocyclothio,
6. when any two of $R_1$–$R_6$ are on the same carbon, they may combine to form an alkylene $CR_{12}R_{13}$, ketone, NOH, $NOC_1$–$C_3$ alkyl, etc.
7. when any two of $R_1$–$R_6$ are on the same carbon, they may combine to form a 3 to 8 member ring which may contain oxygen in addition to carbon, the ring being optionally substituted with one or more $C_1$–$C_4$ alkyl, $C_2$–$C_4$ alkenyl, $OR_7$, $SR_7$, $SOR_{7a}$, $SO_2R_{7a}$, $NR_8R_{8a}$, halogen, cyano or $C_1$–$C_4$ carboalkoxy;

(ii) further in which:
1. $R_7$ comprises H, $C_1$–$C_8$ alkyl, $C_3$–$C_8$ alkenyl, $C_3$–$C_8$ alkynyl, $C_3$–$C_8$ cycloalkyl, $C_5$–$C_8$ cycloalkenyl, $C_3$–$C_8$ alkoxyalkyl, $C_1$–$C_7$COalkyl, $C_1$–$C_6$ CONHalkyl, CONHaryl, $C_1$–$C_4$ CON(alkyl)$_2$, aryl or heterocycle; $R_{7a}$ acomprises $C_1$–$C_8$ alkyl, $C_3$–$C_8$ alkenyl, $C_3$–$C_8$ alkynyl, $C_3$–$C_8$ cycloalkyl, $C_5$–$C_8$ cycloalkenyl, $C_3$–$C_8$ alkoxyalkyl, aryl or heterocycle,
2. $R_8$ comprises $C_1$–$C_7$ COalkyl, $C_1$–$C_6$ CO$_2$alkyl, COaryl, $C_1$–$C_6$ CONHalkyl, CONHaryl, $C_1$–$C_6$ CON(alkyl)$_2$, $C_1$–$C_6$ SO$_2$alkyl, SO$_2$aryl, $C_1$–$C_6$ SO$_2$NHalkyl, SO$_2$NHaryl or $C_1$–$C_7$ SO$_2$N(alkyl)$_2$,
3. $R_{8a}$ comprises H, $C_1$–$C_8$ alkyl, aryl, heterocycle or $C_1$–$C_3$ COalkyl,
4. $R_9$ comprises H, C(O)H, $C_1$–$C_7$ COalkyl, $C_2$–$C_7$ COalkenyl, COaryl, $C_1$–$C_6$CONHalkyl, CONHaryl, CONalkyl$_2$, $C_1$–$C_6$ SO$_2$alkyl, $C_1$–$C_6$ SO$_2$NHalkyl or $C_1$–$C_4$ SO$_2$N(alkyl)$_2$,
5. $R_{10}$ is H or $C_1$–$C_4$ alkyl,
6. $R_{11}$ comprises H, $C_1$–$C_8$ alkyl, $C_2$–$C_8$ alkenyl, $C_3$–$C_8$ cycloalkyl, aryl or heterocycle, and
7. $R_{12}$ and $R_{13}$ are the same or different and comprise H, $C_1$–$C_7$ alkyl, $C_1$–$C_6$ haloalkyl, $C_3$–$C_8$ cycloalkyl, aryl, heterocycle, cyano, $C_1$–$C_6$ carboalkoxy, $C_1$–$C_6$ alkyl-sulfonyl, arylsulfonyl or $C_1$–$C_6$ alkylsulfmyl, or $R_{12}$ and $R_{13}$ being joined in a $C_3$–$C_8$ alkyl ring, (iii) $R_1$–$R_6$ may be the same or different with the provision that at least one of $R_1$–$R_6$ must be different than hydrogen;

(iv) $R_1$–$R_6$ are independently cis or trans to each other and the amide nitrogen, and when n=2 the amide nitrogen is axial or equatorial; and (v) $R_1$–$R_6$ are in any substitution pattern around the alicyclic ring in accordance with chemical bonding rules; and any of the alicyclic rings contain 0–2 endocyclic double bonds, where ring size and substitution pattern allow in accordance with chemical bonding rules, provided that no heteroatoms are bonded to the double bond ring carbons.

The terms alkyl, alkylene, alkenylene and the like, as used herein, include within their scope both straight and branched groups, and the terms alkenyl, alkenylene and the like are intended to include groups containing one or more double bonds. The foregoing terms further contemplate either substituted or unsubstituted forms. A substituted form refers to substitution with one or more groups selected from halo, haloalkoxy, phenyl, alkoxy, carboalkoxy or amido, substituted with one or two alkyl groups.

The terms halogen and halo as used herein include chlorine, bromine, fluorine and iodine. The terms haloalkyl and the like refer to groups substituted with one or more halo atoms. It will be appreciated that certain combinations of substituent groups for compounds which fall within the definitions given herein will be impossible to prepare for steric and/or other chemical reasons. Such compounds are not included within the scope of the invention.

The term 37 aryl" as used herein refers to a phenyl group or naphthyl group optionally substituted with one to three groups independently selected from halo, $C_1$–$C_{10}$ alkyl, branched $C_3$–$C_6$ alkyl, halo $C_1$–$C_7$ alkyl, hydroxy $C_1C_7$ alkyl, $C_1$–$C_7$ alkoxy, halo $C_1$–$C_7$ alkoxy, phenoxy, phenyl, NO$_2$, OH, CN, $C_1$–$C_4$ alkanoyl, benzoyl, $C_1$–$C_4$ alkanoyloxy, $C_1$–$C_4$ alkoxycarbonyl, phenoxycarbonyl, methylenedioxy, or benzoyloxy. Preferred substituents are $C_1$–$C_3$ alkoxy, methylenedioxy, $C_1$–$C_3$ alkylthio, $C_1$–$C_4$ alkyl, $C_1$–$C_4$ haloalkyl, $C_1$–$C_3$ alkoxyalkyl, $C_1$–$C_3$ haloalkoxy or halogen.

The term "heterocycle" refers to thienyl, furyl, tetrahydrofliryl, thiazolyl, benzthiazolyl, quinolinyl, pyrimidyl, pyrazolyl, pyridyl, isoxazolyl, or thienyl, and "substituted heterocycle" refers to the ring system substituted with one to three groups independently selected from halo, $C_1$–$C_{10}$ alkyl, branched $C_3$–$C_6$ alkyl, halo $C_1$–$C_7$ alkyl, hydroxy $C_1$–$C_7$ alkyl, $C_1$–$C_7$ alkoxy, halo $C_1$–$C_7$ alkoxy, phenoxy, phenyl, NO$_2$, OH, CN, $C_1$–$C_4$ alkanoyl, benzoyl, $C_1$–$C_4$ alkanoyloxy, $C_1$–$C_4$ alkoxycarbonyl, phenoxycarbonyl, methylenedioxy, or benzoyloxy. Preferred substituents are $C_1$–$C_3$ alkoxy, methylenedioxy, $C_1$–$C_3$ alkylthio, $C_1$–$C_4$ alkyl, $C_1$–$C_4$ haloalkyl, $C_1$–$C_3$ alkoxyalkyl, $C_1$–$C_3$ haloalkoxy or halogen.

Various hydrates, salts and complexes of compounds of Formula I can be made in the conventional ways. For example, salts may be formed by replacing the hydroxyl hydrogen atom with a cation, for example, $NH_4^+$, $^+N(CH_3)_4$, $^+N(Bu)_4$, $K^+$, $Na^+$, $Ca^{++}$, $Li^+$, $Mg^{2+}$, $Fe^{2+}$, $Cu^{2+}$, etc. These derivatives are also useful in accordance with the present invention.

The designation ( )n in Formula I is used to indicate that the carbocyclic ring of which it is a part can include "n" additional carbon atoms. Accordingly, and for purposes of further definition, it will be appreciated that the Formula I represents acylated aminosalicylamides optionally having a five, six, seven or eight member ring, i.e., n=1, 2, 3 or 4, respectively, as represented by the following Formulae Ia, Ib, Ic and Id:

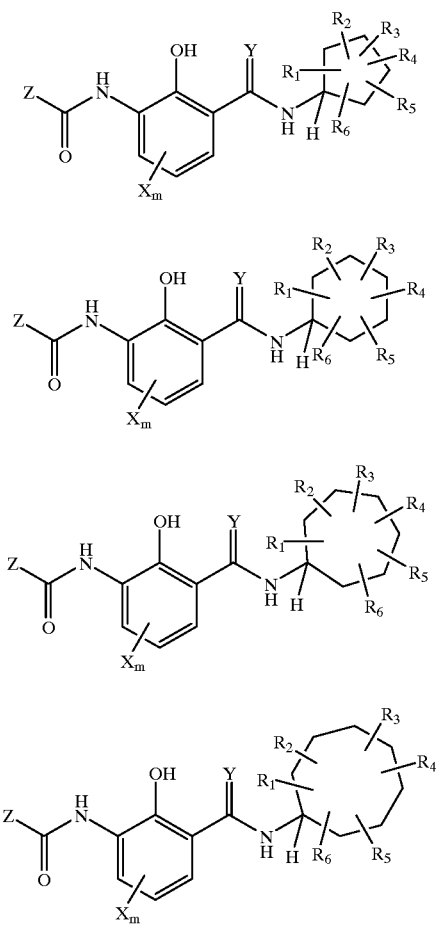

Formula Ia

Formula Ib

Formula Ic

Formula Id

The definitions for the substituent groups, when present, remain the same for each of these embodiments, and the overall formula of the acylated aminosalicylamides is therefore represented by the simplified form of Formula I with n=1–4.

As is apparent from the foregoing descriptions, the AASA compounds are useful in a variety of forms, i.e., with various substitutions as identified. Examples of particularly desirable compounds are quite diverse, and many are mentioned herein. Included are compounds in which Z and/or X are hydrogen, and also those in which each of $R_1$–$R_6$ is selected from the group consisting of hydrogen, $C_1$–$C_4$ alkyl, $C_2$–$C_6$ alkenyl $C_3$–$C_6$ cycloalkyl, aryl, $C_2$–$C_8$ alkoxyalkyl, fiuryl and thienyl. Preferred compounds include those with a spirocyclo group, e.g., a spirocyclopropyl or spirocyclobutyl group. Preferred compounds further include those in which no more than two of the groups $R_1$–$R_6$ is other than hydrogen or methyl, as well as those in which at least two and at most four of the groups $R_1$–$R_6$ are other than hydrogen. The substituent Y is preferably oxygen. The foregoing optional limitations may preferably occur alone or in combination with other identified limitations.

In addition, for the six member ring embodiment in which n=2, further preferred compounds include those in which there are at least two hydrogen groups at the four binding sites at the 2 and 6 positions of the cyclohexyl ring, those in which all of the groups $R_1$–$R_6$ that are other than hydrogen are located at the 3 and 5 positions of the cyclohexyl ring, those in which at least two of the groups $R_1$–$R_6$ are other than hydrogen, and/or those in which four of the groups $R_1$–$R_6$ are other than hydrogen.

For the seven member ring embodiment in which n=3, further preferred compounds include those in which there are at least two hydrogen groups at the four binding sites at the 2 and 7 positions of the cycloheptyl ring, those in which all of the groups $R_1$–$R_6$ that are other than hydrogen are located at the 3, 4, 5 or 6 positions of the cycloheptyl ring, those in which at least two of the groups $R_1$–$R_6$ are other than hydrogen, and/or those in which four of the groups $R_1$–$R_6$ are other than hydrogen.

AASA Compositions

The AASA compounds are preferably applied in the form of a composition comprising one or more of the AASA compounds with a phytologically acceptable carrier. The compositions are either concentrated formulations which are dispersed in water or another liquid for application, or are dust or granular formulations which are applied without further treatment. The compositions are prepared according to procedures which are conventional in the agricultural chemical art, but which are novel and important because of the presence therein of the compounds of this invention. Some description of the formulation of the compositions is given to assure that agricultural chemists can readily prepare desired compositions.

The dispersions in which the compounds are applied are most often aqueous suspensions or emulsions prepared from concentrated formulations of the compounds. Such water-soluble, water suspendable, or emulsifiable formulations are either solids, usually known as wettable powders, or liquids, usually known as emulsifiable concentrates or aqueous suspensions. The present invention contemplates all vehicles by which the acylated aminosalicylamides can be formulated for delivery for use as a fungicide. As will be readily appreciated, any material to which the AASA compounds can be added may be used, provided they yield the desired utility without significant interference with activity of the acylated aminosalicylamides as antifungal agents.

Wettable powders, which may be compacted to form water dispersible granules, comprise an intimate mixture of the active compound, an inert carrier and surfactants. The concentration of the active compound is usually from about 10% to about 90% w/w, more preferably about 25% to about 75% w/w. In the preparation of wettable powder compositions, the toxicant products can be compounded with any of the finely divided solids, such as prophyllite, talc, chalk, gypsum, fuller's earth, bentonite, attapulgite, starch, casein, gluten, montmorillonite clays, diatomaceous earths, purified silicates or the like. in such operations, the finely divided carrier is ground or mixed with the toxicant in a volatile organic solvent. Effective surfactants, comprising from about 0.5% to about 10% of the wettable powder, include sulfonated lignins, naphthalenesulfonates, alkylbenzenesulfonates, alkyl sulfates, and non-ionic surfactants, such as ethylene oxide adducts of alkyl phenols.

Emulsifiable concentrates of the compounds comprise a convenient concentration of the AASA compound, such as from about 10% to about 50% w/w, in a suitable liquid. The compounds are dissolved in an inert carrier, which is either a water miscible solvent or a mixture of water-inmniscible organic solvents, and emulsifiers. The concentrates may be diluted with water and oil to form spray mixtures in the form of oil-in-water emulsions. Useful organic solvents include aromatics, especially the high-boiling naphthalenic and olefinic portions of petroleum such as heavy aromatic naphtha. Other organic solvents may also be used, such as, for example, terpenic solvents, including rosin derivatives, aliphatic ketones, such as cyclohexanone, and complex alcohols, such as 2-ethoxyethanol.

Emulsifiers which can be advantageously employed herein can be readily determined by those skilled in the art and include various nonionic, anionic, cationic and amphoteric emulsifiers, or a blend of two or more emulsifiers. Examples of nonionic emulsifiers useful in preparing the emulsifiable concentrates include the polyalkylene glycol ethers and condensation products of alkyl and aryl phenols, aliphatic alcohols, aliphatic amines or fatty acids with ethylene oxide, propylene oxides such as the ethoxylated alkyl phenols and carboxylic esters solubilized with the polyol or polyoxyalkylene. Cationic emulsifiers include quaternary ammonium compounds and fatty amine salts. Anionic emulsifiers include the oil-soluble salts (e.g., calcium) of alkylaryl sulphonic acids, oil soluble salts or sulphated polyglycol ethers and appropriate saints of phosphated polyglycol ether.

Representative organic liquids which can be employed in preparing the emulsifiable concentrates of the present invention are the aromatic liquids such as xylene, propyl benzene fractions; or mixed naphthalene fractions, mineral oils, substituted aromatic organic liquids such as dioctyl phthalate; kerosene; dialkyl amides of various fatty acids, particularly the dimethyl amides of fatty glycols and glycol derivatives such as the n-butyl ether, ethyl ether or methyl ether of diethylene glycol, and the methyl ether of triethylene glycol. Mixtures of two or more organic liquids are also often suitably employed in the preparation of the emulsifiable concentrate. The preferred organic liquids are xylene, and propyl benzene fractions, with xylene being most preferred. The surface active dispersing agents are usually employed in liquid compositions and in the amount of from 0.1 to 20 percent by weight of the combined weight of the dispersing agent and active compound. The active compositions can also contain other compatible additives, for example, plant growth regulators and other biologically active compounds used in agriculture.

Aqueous suspensions comprise suspensions of water-insoluble compounds of the AASA compounds, dispersed in an aqueous vehicle at a concentration in the range from about 5% to about 50% w/w. Suspensions are prepared by finely grinding the compound, and vigorously mixing it into a vehicle comprised of water and surfactants chosen from the same types above discussed. Inert ingredients, such as inorganic salts and synthetic or natural gums, may also be added to increase the density and viscosity of the aqueous vehicle. It is often most effective to grind and mix the compound at the same time by preparing the aqueous mixture and homogenizing it in an implement such as a sand mill, ball mill, or piston-type homogenizer.

The compounds may also be applied as granular compositions, which are particularly useful for applications to the soil. Granular compositions usually contain from about 0.5% to about 10% w/w of the compound, dispersed in an inert carrier which consists entirely or in large part of coarsely divided attapulgite, bentonite, diatomite, clay or a similar inexpensive substance. Such compositions are usually prepared by dissolving the compound in a suitable solvent and applying it to a granular carrier which has been pre-formed to the appropriate particle size, in the range of from about 0.5 to about 3 mm. Such compositions may also be formulated by making a dough or paste of the carrier and compound, and crushing and during to obtain the desired granular particle.

Dusts containing the compounds are prepared simply by intimately mixing the compound in powdered form with a suitable dusty agricultural carrier, such as, for example, kaolin clay, ground volcanic rock, and the like. Dusts can suitably contain from about 1% to about 10% w/w of the compound.

The active compositions may contain adjuvant surfactants to enhance deposition, wetting and penetration of the compositions onto the target crop and organism. These adjuvant surfactants may optionally be employed as a component of the formulation or as a tank mix. The amount of adjuvant surfactant will vary from 0.01 percent to 1.0 percent v/v based on a spray-volume of water, preferably 0.05 to 0.5 percent. Suitable adjuvant surfactants include ethoxylated nonyl phenols, ethoxylated synthetic or natural alcohols, salts of the esters or sulphosuccinic acids, ethoxylated organosilicones, ethoxylated fatty amines and blends of surfactants with mineral or vegetable oils.

AASA Compositions with Other Compounds

The composition may optionally include fungicidal combinations which comprise at least 1% of one or more of the AASA compounds with another compound. Such additional compounds may be fungicides, herbicides, insecticides, nematocides, miticides, arthropodicides, bactericides or combinations thereof that are compatible with the compounds of the present invention in the medium selected for application, and not antagonistic to the activity of the present compounds. Accordingly, in such embodiments the other pesticidal compound is employed as a supplemental toxicant for the same or for a different pesticidal use. The compounds in combination can generally be present in a ratio of from 1:100 to 100:1.

Utility of AASA Compounds and Compositions as Fungicides

The present invention includes within its scope methods for the control or prevention of fungal attack. These methods comprise applying to the locus of the fungus, or to a locus in which the infestation is to be prevented (for example applying to grape plants), a fungicidal amount of one or more of the AASA compounds or compositions. The AASA compounds are suitable for treatment of various plants at fungicidal levels, while exhibiting low phytotoxicity. The compounds are useful in a protectant or eradicant fashion.

The AASA compounds are applied by any of a variety of known techniques, either as the compounds or as compositions including the compounds. For example, the compounds may be applied to the roots, seeds or foliage of plants for the control of various fungi, without damaging the commercial value of the plants. The materials are applied in the form of any of the generally used formulation types, for example, as solutions, dusts, wettable powders, flowable concentrates, or emulsifiable concentrates. These materials are conveniently applied in various known fashions.

The AASA compounds have been found to have significant fungicidal effect particularly for agricultural use. Many of the compounds are particularly effective for use with agricultural crops and horticultural plants, or with wood, paint, leather or carpet backing.

In particular, the compounds effectively control a variety of undesirable fungi which infect useful plant crops. Activity has been demonstrated for a variety of fungi, including for example the following representative fungal species: Downy Mildew of Grape (*Plasmopara viticola*—PLASVI), Late Blight of Tomato and of Potato (Phytophthora infesians—PHYTIN), Apple Scab (*Venturia inaequalis*—VENTIN), Brown Rust of Wheat (*Puccinia recondita*—PUCCRT), Rice Blast (*Pyricularia oryzae*—PYRIOR), Cercospora Leaf Spot of Beet (*Cercospora beticola*—CERCBE), Powdery Mildew of Wheat (*Erysiphe graminis*—ERYSGT), Leaf Blotch of Wheat (*Septoria tritici*—SEPTTR), Glume Blotch of Wheat (*Septoria nodorum*—LEPTNO), and cultures of *Gloeophyllum trabeum* and *Trametes versicolor*. It will be understood by those in the art that the efficacy of the AASA compounds for the foregoing fungi establishes the general utility of the compounds as fungicides.

The AASA compounds have broad ranges of efficacy as fungicides. The exact amount of the active material to be applied is dependent not only on the specific active material being applied, but also on the particular action desired, the fungal species to be controlled, and the stage of growth thereof, as well as the part of the plant or other product to be contacted with the toxic active ingredient. Thus, all the active ingredients of the AASA compounds, and compositions containing the same, may not be equally effective at similar concentrations or against the same fungal species.

The AASA compounds and compositions are effective in use with plants in a disease inhibiting and phytologically acceptable amount. The term "disease inhibiting and phytologically acceptable amount" refers to an amount of a compound which kills or inhibits the plant disease for which control is desired, but is not significantly toxic to the plant. This amount will generally be from about 1 to about 1000 ppm, with 10 to 500 ppm being preferred. The exact concentration of compound required varies with the fungal disease to be controlled, the type of formulation employed, the method of application, the particular plant species, climate conditions, and the like. A suitable application rate is typically in the range from about 0.10 to about 4 pounds/acre.

Preparation of Compounds
AASA Intermediates

The AASA compounds are preferably produced from corresponding cyclic amines and 3-nitrosalicylamides. In a preferred process. the acylated aminosalicylarnides are obtained by reaction of a 3-aminosalicylaride with acetic-formic anhydride. The 3-aminosalicylamide is prepared by hydrogenation of a 3-nitrosalicylarnide derived from reaction of a 2-hydroxy-3-nitrobenzoyl chloride with the appropriate cyclic arnine. It is therefore an aspect of the present invention to provide the cyclic arnines and 3-nitrosalicylamides which are usefull in preparation of the AASA compounds. In addition, the 3-nitrosalicylarnides and some of the cyclic amnines have fungicidal activity.

A description of the general preparation of the cyclic amines from the corresponding ketones, and the consequent production of the related 3-nitrosalicylamides, is provided hereafter. Partial listings of the amines and 3-nitrosalicylamides are contained in Tables 1 and 2, respectively.

General Preparation of Acylated Aminosalicylamides

A preferred synthesis of the desired product acylated aminosalicylamides (Formula I) is shown in the following Scheme 1. 2-Hydroxy-3-nitrobenzoic acid 1 was converted to the acid chloride 2 with excess thionyl chloride. After removal of the excess thionyl chloride, the crude acid chloride 2 was reacted with the desired cyclic amine 3 in dichloromethane solution containing triethylamine as an acid scavenger and 4-dimethylaminopyridine (DMAP) as a catalyst. Crude 3-nitrosalicylamide 4 could be isolated after washing the reaction mixture with dilute HCl solution, drying, and evaporation of the solvent. Usually 4 was of sufficient purity to carry forward to the final product 6, but if desired could be purified by recrystallization or chromatography or a combination of both. In some cases where the 3-nitrosalicylamide 4 is a mixture of diastereomers, one might choose to isolate the individual diastereomers at this stage. However, since all of the various diastereomers are fuigicidally active, this is not necessary. The 3-nitrosalicylamide (4) was subsequently reduced under catalytic hydrogenation conditions using Pd, Pt, or Ni catalysts either unpoisoned or poisoned with sulfur or lead. The 3-aminosalicylamide 5 usually was not isolated, but immediately reacted with excess acetic-formic anhydride. Isolation of the AASA product 6 was a simple matter of filtration, washing with sodium bicarbonate solution, drying and evaporation of the solvent The crude product 6, usually a solid foam or glass, often was of sufficient purity to be directly submitted for testing. However, if desired, it could be further purified by recrystallization or chromatography or a combination of both.

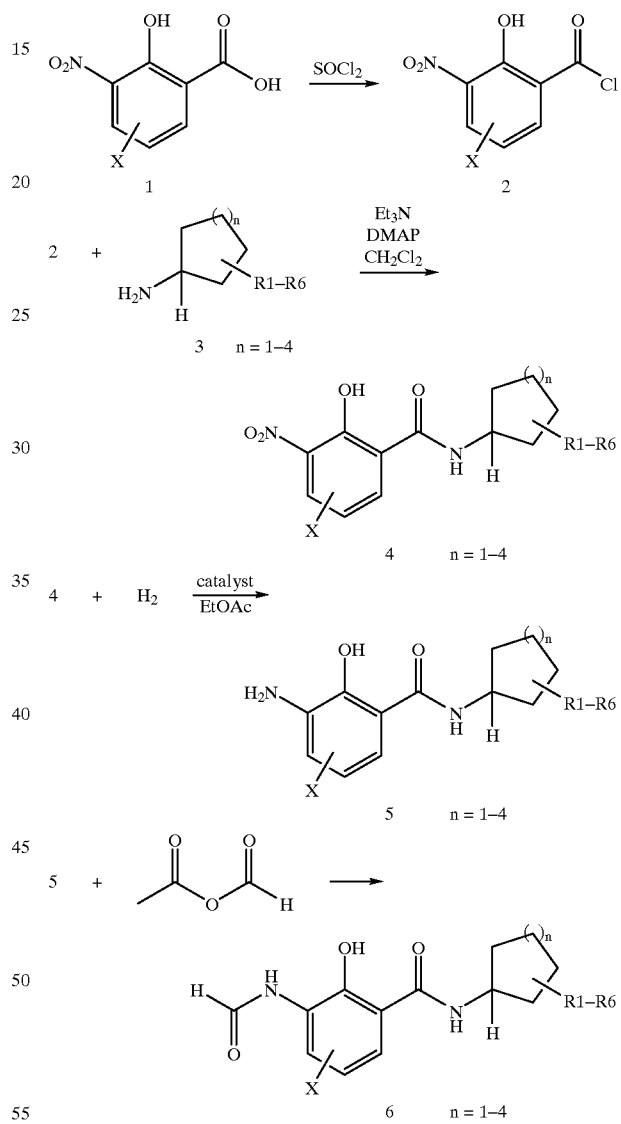

Scheme 1

The following discussion presents a description of sample preparations of the AASA compounds of the present invention based upon the foregoing Scheme 1, wherein X, ( )n, and $R_1$–$R_6$ are as defined in Formula I. Throughout this discussion, all temperatures are given in degrees Celsius and all percentages are weight percentages unless otherwise stated.

Obtaining Compound 1

Preparation of 5-Chloro-3-nitrosalicylic acid

The following procedure demonstrates the preparation of compound 1 with X=5–Cl, with comparable procedures being useful for obtaining related compounds having different X. A solution suspension of 10 g of 5-chlorosalicylic acid in 50 ml glacial acetic acid was cooled in an ice bath until the solvent began to freeze. The bath was exchanged to a room temperature water bath and 4.47 g of 90% fuming nitric acid (1:1 equivalent) in 3 ml glacial acetic acid was added dropwise. After addition was complete, the mixture was stirred for 150 minutes at room temperature (R. T.) in the water bath. It was then poured into 120 ml of ice. and water and stirred in an ice bath for 30 minutes. The precipitated solid was collected by filtration and air-dried overnight.

The crude solid was recrystallized from ethanol-water to give 7.86 g of light yellow crystals. This solid was then recrystallized from toluene to give 5.82 g of light yellow needles (m. p. 162–166°).

Converting 1 to 2

Preparation of 2-Hydroxy-3-nitrobenzoyl chloride

2-Hydroxy-3-nitrobenzoic acid (1, 3-nitrosalicylic acid) was used as obtained from TCI America. A mixture of 3-nitrosalicylic acid (3.46 g), thionyl chloride (10 ml), and N,N-dimethylformamide (3 drops) was stirred and heated at 75° until a homogeneous solution resulted and gas evolution ceased (approximately 20 minutes). Excess thionyl chloride was removed on a rotary evaporator. 1,2-Dichloroethane (30 ml) was added to the yellow residue and the volatiles again removed via rotary evaporation. This was repeated a second time to ensure complete removal of all thionyl chloride. The yellow residual 2-hydroxy-3-nitrobenzoyl chloride (2, X=H) was used immediately in subsequent condensations with amines. The yield was assumed to be quantitative (3.83 g). A similar procedure yields the counterpart products where the 2-hydroxy-3-nitrobenzoic acid has various X substituents.

Preparation of Cyclic Amines

General Preparation of Intermediate Cyclic Amines

Scheme 2

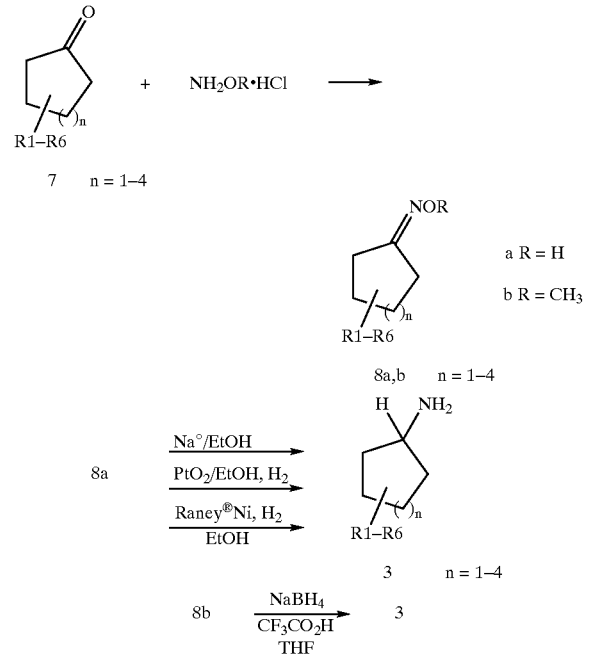

Preparation of most of the requisite cyclic amines can be achieved by converting the appropriately substituted cyclic ketone to either the oxime (8a) or the methyl oxime (8b) as shown in Scheme 2. The resultant oximes (8a, 8b) are often a mixture of E and Z isomers. Conversion of the oximes 8a to the desired cyclic amnines 3 can be achieved by use of sodium in boiling ethanol, or catalytically using either platinum oxide or Raney® nickel as a catalyst. Alternatively, the methyl oxime can be reduced using sodium borohydride/ trifluoracetic acid in THF as described in N. Umino, T. Iwakuma, M. Ikezaki, M. Itoh, Chem. Pharm. Bull., 1978, 26, 2897.

Regardless of the reduction method, the product amines were often obtained as a mixture of diastereomers. While it was sometimes possible to separate these diastereomers either at the amine stage (through derivatization or recrystallization of various salts), at the intermediate 3-nitrosalicylamide (4) stage, or at the final AASA product (6) stage, separation was not essential since the final product (6) resulting from each diastereomer whether in the pure form or in mixtures with other diastereomers was biologically active.

The procedures described below are typical examples of the general procedures used to prepare the necessary intermediates. They may be easily scaled up or down as needed by one skilled in the art.

General Preparation of Intermediate Cyclic Ketones

Large numbers of cyclopentanones, cyclohexanones, cycloheptanones and cyclooctanones are well described in the chemical literature. Some useful preparative procedures for forming $C_5$, $C_6$, $C_7$ and $C_8$ cyclic ketones can be found in P. A. Aristoff and C. L. Nelson, Organic Preparations and Procedures Int, 1983, 15, 149; A. L. Lieberman and J. V. Vasima, Zhurnal Organicheskoi Khimii, 1967, 3, 690; E. C. Homing, M. O. Denekas, and R. E. Field, J. Org. Chem, 1944, 9, 547; E. W. Garbish, Jr., J. Org. Chem, 1965, 30, 2109; Karl H. Segel, Chem. Ber., 1960, 93, 2529; Heinz, E. Adams, R. Klintz, and P. Welzel, Tetrahedron, 1990, 46 (12) 4217–30; M. St. Jacques and C. Vazirir, Can. J. Chem., 1973, 51 (8), 1192–9; and Challand, B. D. et al. J. Org. Chem., 1969, 34, 794. Many useful intermediates such as isophorone. 3-methyl-2-cyclohexen-1-one, 3,5-dimethyl-2-cyclohexen-1-one, 2-methyl-2-cyclopenten-1-one, 3-methyl-2-cyclopenten-1-one, 2-cyclohepten-1-one, dimedone and 1,4-cyclohexanedione mono-ethylene ketal are commercially available, for example from Aldrich Chemical Co., Milwaukee, Wis. USA. Preparative methods for carrying out 1,4-additions to cyclic enones can be found in S. Matsuzawa, Y. Horiguchi, E. Nakamura, 1. Kuwajima, Tetrahedron, 1989, 45, 349; J. Kabbara, S. Flemming, K. Nickisch, H. Neh, J. Westerman, Tetrahedron, 1995, 51, 743; C. R. Johnson and T. J. Marren, Tetrahedron Lett., 1987, 28, 27; and B. H. Lipshutz, R. S. Wilhelm, and J. A. Kozlowski, J. Org. Chem., 1984, 49, 3938. Herbert O. House, Modem Synthetic Reactions, $2^{nd}$ Ed., W. A. Benjaman, Inc., Menlo Park, Calif., 1972, Chapters 8,9 is particularly useful for developing procedures for aklation and halogenation of cyclic ketones.

The preparations of various ketones useful in accordance with the present inventions are known in the art, and are exemplified by the foregoing literature references, which are hereby incorporated by reference. The following procedure demonstrates the preparation of a spiroketone.

Preparation of 7,7-dimethylspiro[2.5]octane-5-one

By the method of Weedon (Rudolph, A., Weedon, A. C., J. Am. Chem. Soc., 1989 (111) 875–8757) isophorone (8.0 mL, 52.7 mmol) was dissolved in 500 mL ethyl acetate and 0.2 mL acetic acid was added. This solution was continuously purged with a slow stream of nitrogen and subjected to photolysis with 450 watt medium pressure lanip through a Pyrex filter for 24 hr to give the exocyclic alkene. The solvent was removed on The rotovap with a bath temperature below 25° C. and the residue was dissolved in 30 mL of ethyl ether and added dropwise to a stirred solution of lithiun aluminum hydride (3.0 g, 79 mmol) in 150 mL of ethyl ether. The reaction was heated to reflux for 20 min, then cooled in an ice bath and 3.0 mL water was added slowly, followed by 3.0 mL of 15% sodium hydroxide, then 9 mL water. The resulting slurry was stirred for 10 min., then filtered and the filter cake rinsed with ethyl ether. The filtrate was evaporated to give a viscous oil, which was evaporatively distilled (pot temp 65° C. @ 0.75 torr) to give 4.6 g of 3,3-dimethyl-5-methylenecyclohexan-1-ol as a white waxy solid, 95% pure by GLC.

The above cyclohexanol (1.85 g, 13.21 mmol) was dissolved in 60 mL benzene and diethyl zinc (53 mL of 1 M solution in hexanes, 53 mmol) was added. The mixture was heated to 60° C. and diiodomethane (4.3 mL, 53 mmol) was added in one portion, followed by stirring at 60° C. for 24 hr. The reaction was cooled, 20 mL sat'd ammonium chloride and 20 mL sat'd sodium thiosulfate were added and the mixture stirred for 30 min. The phases were separated and the organic phase worked up in the normal manner. In order to facilitate the separation of the spiro alcohol from starting olefin, the crude product was subjected to epoxidation by dissolving in 60 mL of dichloromethane and cooling to 10° C. then m-chloroperbenzoic acid (50–75%, 4 g) was added. The mixture was stirred at 0° C. until reaction complete, then quenched by the addition of 20 mL sat'd sodium sulfite solution. The organic phase was worked up with sodium bicarbonate in the usual fashion and the crude product purified by radial chromatography eluting with 75% hexane/25% ethyl acetate to give 300 mg of the desired alcohol. This was oxidized in 20 mL of dichloromethane using 3 e(luiv. of Dess-Martin reagent at room temperature for 5 hr, worked up in the usual manner and purified by radial chromatography eluting with 85% hexane/15% ethyl acetate to give 235 mg of pure ketone as an oil, M/Z=152.

Preparation of 5-Ethyl-3,3,5-trimethylcyclohexyloxime

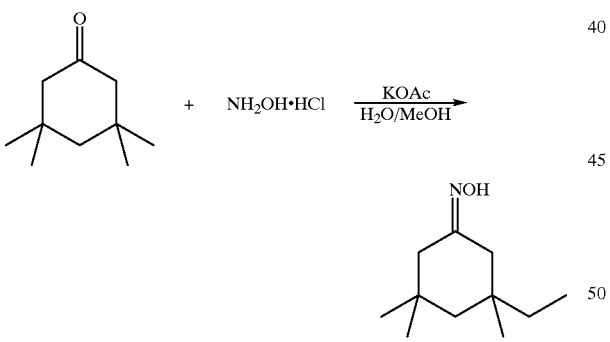

To a stirred solution of 3-ethyl-3,5,5-trimethylcyclohexanone (11.78 g) in methanol was added all at once a solution of hydroxylamine hydrochloride (6.95 g) and potassium acetate (9.81 g) in water (75 ml). The resulting mixture was heated at reflux for 20 minutes, then stirred at room temperature overnight. Water (400 ml) was added and the resulting mixture extracted with ether (3×125 ml). The ether extracts were combined, washed with saturated sodium bicarbonate solution (100 ml), dried (MgSO$_4$) and the solvent evaporated to give the desired product. Proton NMR (CDCl$_3$) showed that the product was a mixture of E and Z isomers. Analysis by gas chromatography/ mass spectrum (GC/MS) showed that this material had the correct m/e for the parent ion.

Preparation of 5-Ethyl-3,3,5-trimethylcyclohexylamine

Platinum Oxide Method

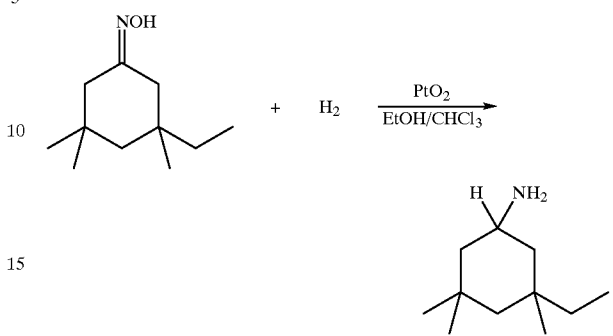

To a solution of 5-ethyl-3,3,5-trimethylcyclohexyloxime (1.83 g,. 01 mole) and trichloromethane (1 ml) in ethanol (50 ml) contained in a 300 ml Parr pressure bottle was added platinum oxide (0.5 g). The resulting mixture was subjected to a hydrogen atmosphere (initial hydrogen pressure=50 psi) until hydrogen uptake ceased (6–8 hours). Gas chromatography showed that all of the oxime had been consumed. The reaction mixture was filtered and the solvent evaporated. The residual HCl salt was taken up in water (25 ml), washed with ether (25 ml) and the organic phase discarded. The aqueous phase was made strongly basic by adding 50% sodium hydroxide solution (2 ml). The resulting mixture was extracted with ether (2×50 ml), the ether extracts combined, dried (Na$_2$SO$_4$) and the solvent evaporated to give a nearly colorless oil (1.26 g). The proton NMR (CDCl$_3$) and GC/NIS were consistent with this being a 63:37 mixture of diastereomers.

Preparation of 5-Cyclopropyl-3,3,5-trimethylcyclohexylamine

Raney® Nickel Method.

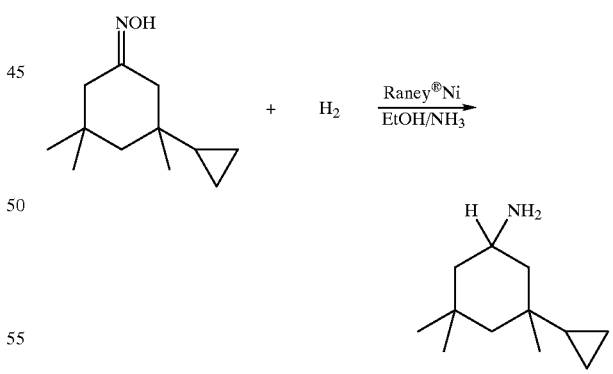

Raney® Nickel (35 g wet weight, Aldrich Chemical Co.) in a 2L Parr pressure bottle was washed with water (3×150 ml) then ethanol (3×100 ml), the wash solvent being decanted each time. To this washed catalyst was added a solution of 5-cyclopropyl-3,3,5-trimethylcyclohexyloxime (32 g) in anhydrous ethanol (350 ml). The resulting mixture was saturated with ammonia by bubbling ammonia gas through the solution for 5 minutes. This solution was placed under a hydrogen atmosphere (initial hydrogen pressure=50 psi) on a Parr shaker. After hydrogen uptake ceased (4–6 hours), gas chromatography showed that the starting oximes had been consumed and replaced by two closely spaced more volatile materials (62:38 ratio). The reaction mixture was filtered, poured into water (1500 ml), and extracted with pentane (3×200 ml). The pentane extracts were combined, washed with saturated sodium chloride solution (200 ml), dried (Na$_2$SO$_4$) and the solvent evaporated to yield a nearly colorless liquid (27.4 g). The proton NMR (CDCl$_3$) and GCIMS was consistent with this material being a diastereomeric mixture of the desired amines. This material was used directly without additional purification.

Preparation of 3,3,4,4-Tetramethylcyclopentylamine

Sodium in Ethanol Method

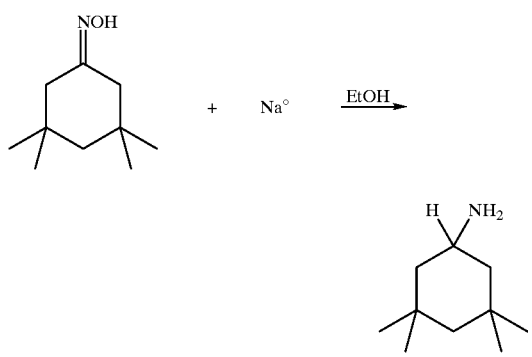

To a solution of 3,3,4,4-tetramethylcyclopentyloxime (5.00 g,. 032 mole) in boiling ethanol (150 ml) was carefuilly added over a 30 minute period sodium spheres (approximately 12 g). After the addition was complete, the reaction mixture was heated at reflux until all of the sodium. had reacted (about 1 hour). Gas chromatography showed that all of the oxime had reacted and was replaced by essentially a single product. Ice water (600 ml) was carefully added and the resulting mixture extracted with pentane (3×150 ml). The pentane extracts were combined, washed with saturated sodium chloride solution (100 ml), dried (Na$_2$SO$_4$), and the solvent carefully evaporated to give a white oily solid (4.4 g). The proton NMR (CDCl$_3$) and GC/MS were consistent with this being essentially pure 3,3,4,4-tetramethylcyclopentylamine Preparation of O-Methyl-3-(furan-2-yl)-5,5-dimethylcylohexyl-oxime

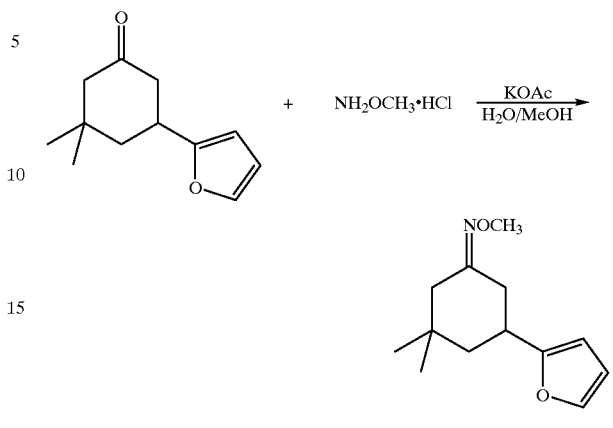

To a stirred solution of 3-(furan-2-yl)-5,5-dimethylcylohexanone (9.2 g, 0.048 mole) in methanol (75 ml) was added all at once a solution of methoxylamine hydrochloride (6.26 g,. 075 mole) and potassium acetate (7.36 g,. 075 mole) in water (75 ml). The resulting mixture was heated at reflux for 20 minutes, then stirred at room temperature for 12 hours. The reaction mixture was diluted with water (400 ml) then extracted with ether (2×200 ml). The ether extracts were combined, washed with saturated sodium bicarbonate solution (100 ml), stirred with activated charcoal, filtered, dried (MgSO$_4$) and the solvent evaporated to give the oxime as a colorless oil (9.1 g). Proton NMR (CDCl$_3$) clearly indicated that this was a 50:50 mixture of E and Z isomers. Analysis by GC/MS showed that this material had the correct m/e for the parent ion.

Preparation of Cyclic Amines from the Methyl Oxime

Sodium Borohydride/Trifluoracetic Acid Method

The methyl oxime is reduced using sodium borohydride/ trifluoracetic acid in THF in accordance with the procedure set forth in N. Umino, T. Iwakuma, M. Ikezaki, M. ltoh. *Chem. Pharm. Buli.*, 1978, 26, 2897.

Based upon the foregoing Scheme 2 and representative examples, the following cyclic amines listed in Table 1 were prepared:

TABLE 1

| Compound Number | Melting Point (° C.) | Molecular Ion (M) | Salt | Amine |
|---|---|---|---|---|
| 101 | | | HCl | H$_2$N–⬡–⬡ |
| 102 | | | HCl | H$_2$N–⬡ (tetramethyl) |

TABLE 1-continued
| Compound Number | Melting Point (° C.) | Molecular Ion (M) | Salt | Amine |
|---|---|---|---|---|
| 103 | | | HCl | 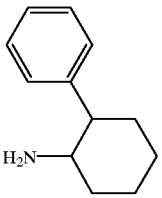 |
| 104 | | | | 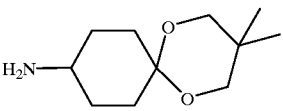 |
| 105 | | | | 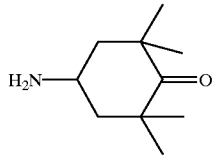 |
| 106 | | | HCl | 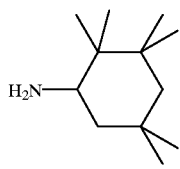 |
| 107 | >260 | | HCl | 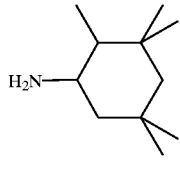 |
| 108 | | | HCl | 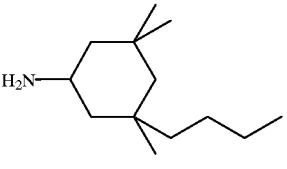 |
| 109 | 290–300 | | HCl | 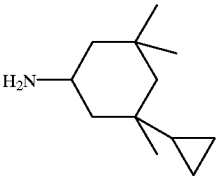 |
| 110 | | | HCl | 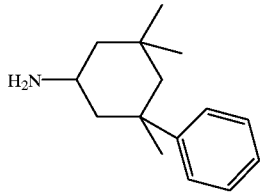 |

TABLE 1-continued

| Compound Number | Melting Point (° C.) | Molecular Ion (M) | Salt | Amine |
|---|---|---|---|---|
| 111 | | | HCl | 3,3,5-trimethylcyclohexylamine |
| 112 | sublimes | | HCl | 3-butyl-3-methylcyclohexylamine (approx.) |
| 113 | | 235 | HCl | 3,5-bis(trifluoromethyl)cyclohexylamine |
| 114 | | | | 3-tert-butyl-5,5-dimethylcyclohexylamine |
| 115 | | | | cis-3,5-dimethylcyclohexylamine (stereo) |
| 116 | | | | 3,5-dimethylcyclohexylamine (stereo) |
| 117 | | | | 3,3,5-trimethyl-5-isopropylcyclohexylamine |

TABLE 1-continued

| Compound Number | Melting Point (° C.) | Molecular Ion (M) | Salt | Amine |
|---|---|---|---|---|
| 118 | | | | (structure) |
| 119 | | 170 | | (structure) |
| 120 | | | | (structure) |
| 121 | | | | (structure) |
| 122 | | | HCl | (structure) |
| 123 | | | | (structure) |
| 124 | | | | (structure) |

TABLE 1-continued

| Compound Number | Melting Point (° C.) | Molecular Ion (M) | Salt | Amine |
|---|---|---|---|---|
| 125 | | | | 5-amino-1,3,3-trimethylcyclohexyl methyl ether derivative |
| 126 | | | | 5-amino-1,3,3-trimethylcyclohexanemethyl methyl ether (stereoisomer) |
| 127 | | | | 5-amino-1,3,3-trimethylcyclohexyl-(2,2-dimethyloxiranyl) |
| 128 | | | | 3-isopropyl-5-methylcyclohexylamine |
| 129 | | | | 3-isopropyl-5-methylcyclohexylamine (stereoisomer) |
| 130 | | | | 5-amino-1,3,3-trimethyl-1-phenylcyclohexane |
| 131 | | | | 3-methyl-5-phenylcyclohexylamine |

TABLE 1-continued
| Compound Number | Melting Point (° C.) | Molecular Ion (M) | Salt | Amine |
|---|---|---|---|---|
| 132 | | | | 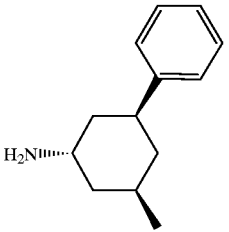 |
| 133 | | | | 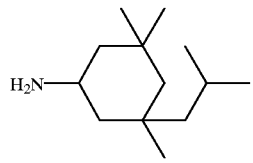 |
| 134 | | | | 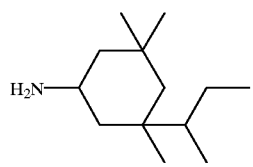 |
| 135 | | 169 | | 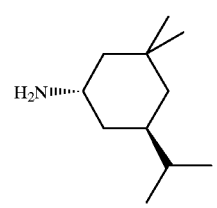 |
| 136 | | 169 | | 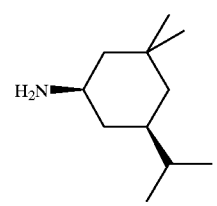 |
| 137 | | 169 | | 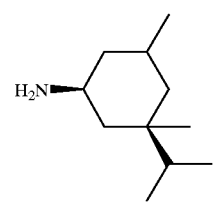 |
| 138 | | 248 | | 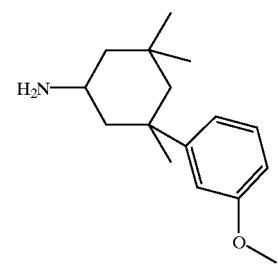 |

TABLE 1-continued

| Compound Number | Melting Point (° C.) | Molecular Ion (M) | Salt | Amine |
|---|---|---|---|---|
| 139 | 157–161 | | | |
| 140 | | | | |
| 141 | | 190 | | |
| 142 | | | | |
| 143 | | M + H 232 | | |
| 144 | | | | |
| 145 | | | | |

TABLE 1-continued

| Compound Number | Melting Point (° C.) | Molecular Ion (M) | Salt | Amine |
|---|---|---|---|---|
| 146 | | 169 | HCl | |
| 147 | | | | |
| 148 | | | | |
| 149 | | 184 | HCl | |
| 150 | | 217 | HCl | |
| 151 | | M − H 246 | | |

TABLE 1-continued

| Compound Number | Melting Point (° C.) | Molecular Ion (M) | Salt | Amine |
|---|---|---|---|---|
| 152 | | M − H 246 | | |
| 153 | | | | |
| 154 | | 183 | HCl | |
| 155 | | 183 | | |
| 156 | | 193 | | |
| 157 | | 198 | HCl | |

TABLE 1-continued

| Compound Number | Melting Point (° C.) | Molecular Ion (M) | Salt | Amine |
|---|---|---|---|---|
| 158 | | 231 | HCl | |
| 159 | | 141 | | |
| 160 | | | | |
| 161 | | | HCl | |
| 162 | | 155 | | |
| 163 | | 211 | HCl | |
| 164 | | 217 | HCl | |

TABLE 1-continued

| Compound Number | Melting Point (° C.) | Molecular Ion (M) | Salt | Amine |
|---|---|---|---|---|
| 165 | | 192 | | |
| 166 | | | HCl | |
| 167 | | | | |
| 168 | | | | |
| 169 | | | | |
| 170 | | | | |
| 171 | | 167 | | |
| 172 | | 161 | | |

TABLE 1-continued

| Compound Number | Melting Point (° C.) | Molecular Ion (M) | Salt | Amine |
|---|---|---|---|---|
| 173 | | M + H 156 | HCl | |
| 174 | | 167 | | |
| 175 | | 99 | | |
| 176 | | | | |
| 177 | >350 | 169 | HCl | |
| 178 | | 127 | HCl | |
| 179 | | | | |
| 180 | | 141 | | |
| 181 | | M − H 260 | | |

TABLE 1-continued
| Compound Number | Melting Point (° C.) | Molecular Ion (M) | Salt | Amine |
|---|---|---|---|---|
| 182 | | 261 | | 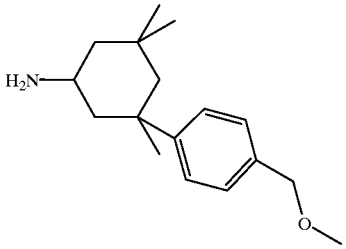 |
| 183 | | | | 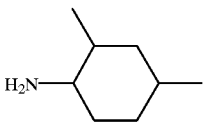 |
| 184 | | 245 | | 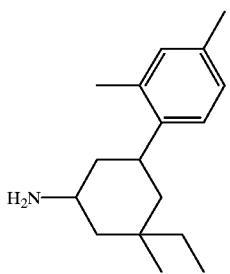 |
| 185 | | 155 | | 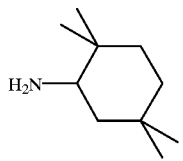 |
| 186 | 266–269 | M + H 170 | HCl | 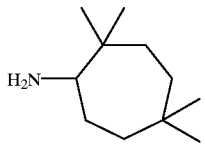 |
| 187 | >325 | M + H 170 | HCl | 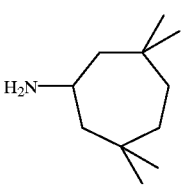 |
| 188 | | 195 | | 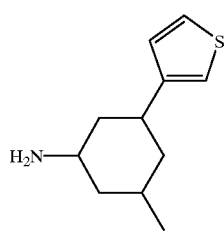 |

TABLE 1-continued

| Compound Number | Melting Point (° C.) | Molecular Ion (M) | Salt | Amine |
|---|---|---|---|---|
| 189 | | | | (structure: 5-amino-1,3,3-trimethylcyclohexyl methyl group bonded to N(CH₃)–C(=O)–phenyl) |
| 190 | | M + H 172 | | (structure: 4-amino-2,2,6,6-tetramethylcyclohexan-1-ol) |
| 191 | | M + H 224 | | (structure: 5-amino-3-ethyl-3-methylcyclohexyl substituted with thiophen-3-yl) |
| 192 | | M + H 266 | | (structure: 5-amino-cyclohexane with two phenyl substituents, stereochemistry shown) |
| 193 | | | | (structure: 4-amino-2,2,6,6-tetramethyl-1-phenylcyclohexan-1-ol) |
| 194 | 127 | | | (structure: 2,2-dimethylcyclohexylamine) |

TABLE 1-continued

| Compound Number | Melting Point (° C.) | Molecular Ion (M) | Salt | Amine |
|---|---|---|---|---|
| 195 | | | | (structure) |
| 196 | | | | (structure) |
| 197 | | | | (structure) |
| 198 | | | | (structure) |
| 199 | | | | (structure) |
| 200 | | | | (structure) |
| 201 | | | | (structure) |
| 202 | | 141 | HCl | (structure) |

TABLE 1-continued

| Compound Number | Melting Point (° C.) | Molecular Ion (M) | Salt | Amine |
|---|---|---|---|---|
| 203 | | | | (structure) |
| 204 | | | | (structure) |
| 205 | | | | (structure) |
| 206 | | | HCl | (structure) |
| 207 | | | | (structure) |
| 208 | | | | (structure) |
| 209 | | | | (structure) |

TABLE 1-continued
| Compound Number | Melting Point (° C.) | Molecular Ion (M) | Salt | Amine |
|---|---|---|---|---|
| 210 | | 169 | | 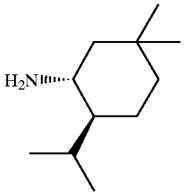 |
| 211 | | | | 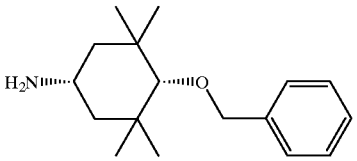 |
| 212 | | | | 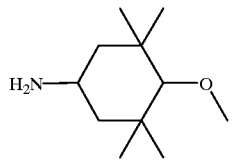 |
| 213 | | | | 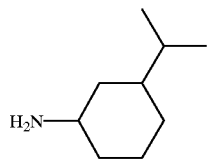 |
| 214 | | | | 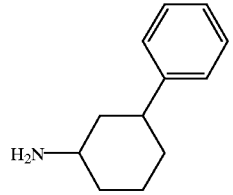 |
| 215 | | | | 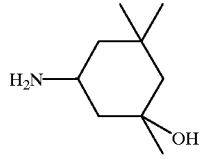 |
| 216 | | 183 | | 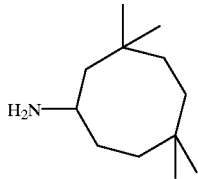 |

TABLE 1-continued

| Compound Number | Melting Point (° C.) | Molecular Ion (M) | Salt | Amine |
|---|---|---|---|---|
| 217 | | 183 | | |
| 218 | | | | |
| 219 | | 245 | | |
| 220 | | | | |
| 221 | | 181 | HCl | |
| 222 | >325 | 183 | HCl | |
| 223 | | | | |

TABLE 1-continued

| Compound Number | Melting Point (° C.) | Molecular Ion (M) | Salt | Amine |
|---|---|---|---|---|
| 224 | | | HCl | |
| 225 | | | | |
| 226 | | | | |
| 227 | | | | |
| 228 | 293 | 155 | HCl | |
| 229 | | | | |
| 230 | | | | |

TABLE 1-continued

| Compound Number | Melting Point (° C.) | Molecular Ion (M) | Salt | Amine |
|---|---|---|---|---|
| 231 | | | | |
| 232 | | | | |
| 233 | | | | |
| 234 | | | | |
| 235 | | 167 | | |
| 236 | | 189 | HCl | |
| 237 | | | | |

TABLE 1-continued

| Compound Number | Melting Point (° C.) | Molecular Ion (M) | Salt | Amine |
|---|---|---|---|---|
| 238 | 252 | 187 | HCl | |
| 239 | >300 | | HCl | |
| 240 | | | | |
| 241 | | | | |
| 242 | | | | |
| 243 | | 227 | | |

Preparing the 3-Nitrosalicylamide

Preparation of N-(3-ethyl-3,5,5-trimethylcyclohexyl)2-hydroxy-3-nitrobenzamide

To a stirred soution of 3-ethyl-3,5,5-trimethylcyclohexylamine (3.20 g, a 6:4 mixture of axial:equatorial ethyl diastereomers), triethylamine (2.13 g) and 4-dimethylaminopyridine (DMAP) (0.12 g) in dichloromethane (50 ml) was added, in a rapid dropwise manner, a solution of 2-hydroxy-3-nitrobenzoyl chloride (3.83 g) in dichloromethane (10 ml). After the addition was complete, the reaction mixture was stirred at room temperature for 12 hours, then poured into 1N HCl (250 ml). The organic layer was separated, and the aqueous layer washed with dichloromethane (50 ml). The organic phases were combined, dried (MgSO$_4$) and the solvent evaporated to give a yellow solid (5.70 g). Recrystallization from methanol gave an analytical sample (m.p. 125–128° C.). The $^{13}$C NMR of this material showed it to be a mixture of diastereomers in an approximate ratio of 6:4.

The foregoing procedure was used with corresponding cyclic amines, as exemplified in Table 1, to prepare the following 3-nitrosalicylamides listed in Table 2:

TABLE 2
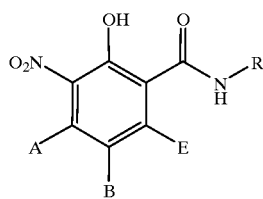
Note: Left most bond on R indicates linking bond to NH in structure above.
| Compound Number | Melting Point (° C.) | Molecular Ion (M) | A | B | E | R |
|---|---|---|---|---|---|---|
| 301 | 109–112 138–145 | | H | H | H | |
| 302 | 201–203 | | H | H | H | |
| 303 | 157–159 | | H | H | H | |
| 304 | 108–110 | | H | H | H | |
| 305 | | 362 | H | H | H | |
| 306 | 115–118 | | H | Cl | H | |
| 307 | | | H | H | H | |
| 308 | 151–155 | 348 | H | H | H | |

TABLE 2-continued
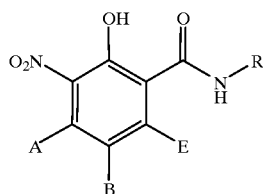
Note: Left most bond on R indicates linking bond to NH in structure above.
| Compound Number | Melting Point (° C.) | Molecular Ion (M) | A | B | E | R |
|---|---|---|---|---|---|---|
| 309 | 117–121 | | H | H | H | |
| 310 | | | H | H | H | |
| 311 | | | H | H | H | |
| 312 | | | H | H | H | |
| 313 | | | H | H | H | |
| 314 | | | H | H | H | |

TABLE 2-continued
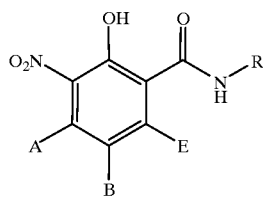
Note: Left most bond on R indicates linking bond to NH in structure above.
| Compound Number | Melting Point (° C.) | Molecular Ion (M) | A | B | E | R |
|---|---|---|---|---|---|---|
| 315 | 181–183 | | H | H | H | |
| 316 | | | H | H | H | |
| 317 | 183–184 | | H | H | H | |
| 318 | 186–190 | | H | H | H | |
| 319 | | | H | H | H | |
| 320 | | | H | H | H | |

TABLE 2-continued
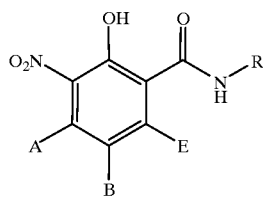
Note: Left most bond on R indicates linking bond to NH in structure above.
| Compound Number | Melting Point (° C.) | Molecular Ion (M) | A | B | E | R |
|---|---|---|---|---|---|---|
| 321 | 125–128 | | H | H | H | |
| 322 | 170–171.5 | | H | H | H | |
| 323 | 187–189 | | H | H | H | |
| 324 | 185–187 | | H | H | H | |
| 325 | | | H | H | H | |
| 326 | 140–150 | | H | H | H | |

TABLE 2-continued
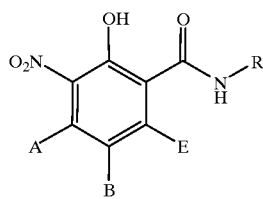
Note: Left most bond on R indicates linking bond to NH in structure above.
| Compound Number | Melting Point (° C.) | Molecular Ion (M) | A | B | E | R |
|---|---|---|---|---|---|---|
| 327 | | | H | H | H | |
| 328 | | | H | H | H | |
| 329 | | | H | H | H | |
| 330 | 134–135.5 | | H | H | H | |
| 331 | | | H | H | H | |
| 332 | | | H | H | H | |

TABLE 2-continued
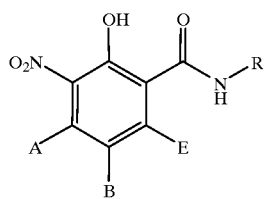
Note: Left most bond on R indicates linking bond to NH in structure above.
| Compound Number | Melting Point (° C.) | Molecular Ion (M) | A | B | E | R |
|---|---|---|---|---|---|---|
| 333 | | | H | H | H | |
| 334 | | | H | H | H | |
| 335 | 153–156 | | H | H | H | |
| 336 | | | H | H | H | |
| 337 | | | H | H | H | |
| 338 | | M + H 363 | H | H | H | |

TABLE 2-continued
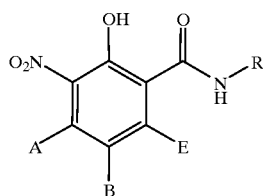
Note: Left most bond on R indicates linking bond to NH in structure above.
| Compound Number | Melting Point (° C.) | Molecular Ion (M) | A | B | E | R |
|---|---|---|---|---|---|---|
| 339 |  | M + H 335 | H | H | H |  |
| 340 | 101–105 |  | H | H | H |  |
| 341 | 140–142 |  | H | H | H |  |
| 342 |  | 412 | H | H | H |  |
| 343 |  |  | H | H | H |  |

TABLE 2-continued
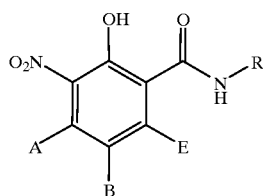
Note: Left most bond on R indicates linking bond to NH in structure above.
| Compound Number | Melting Point (° C.) | Molecular Ion (M) | A | B | E | R |
|---|---|---|---|---|---|---|
| 344 | | 368 | H | H | H | |
| 345 | | M + H 356 | H | H | H | |
| 346 | | 355 | H | H | H | |
| 347 | 68–70 | M − H 395 | H | H | H | |
| 348 | | | H | H | H | |

TABLE 2-continued
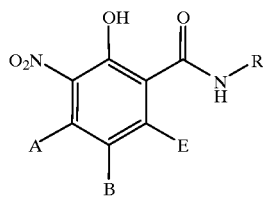
Note: Left most bond on R indicates linking bond to NH in structure above.
| Compound Number | Melting Point (° C.) | Molecular Ion (M) | A | B | E | R |
|---|---|---|---|---|---|---|
| 349 | | | H | H | H | |
| 350 | 101–103 | | H | H | H | |
| 351 | | | H | H | H | |
| 352 | | | H | H | H | |
| 353 | | | H | H | H | |
| 354 | | 349 | H | H | H | |

TABLE 2-continued
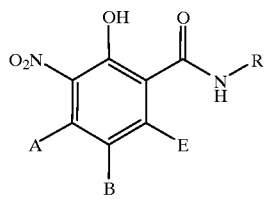
Note: Left most bond on R indicates linking bond to NH in structure above.
| Compound Number | Melting Point (° C.) | Molecular Ion (M) | A | B | E | R |
|---|---|---|---|---|---|---|
| 355 | | 382 | H | H | H | |
| 356 | 117–119 | | H | H | H | |
| 357 | | | H | H | H | |
| 358 | | | H | H | H | |
| 359 | 104–106 | 348 | H | H | H | |

TABLE 2-continued
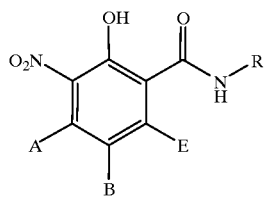
Note: Left most bond on R indicates linking bond to NH in structure above.
| Compound Number | Melting Point (° C.) | Molecular Ion (M) | A | B | E | R |
|---|---|---|---|---|---|---|
| 360 | | M − H 347 | H | H | H | |
| 361 | | | H | H | H | |
| 362 | 110–112 | | H | H | H | |
| 363 | 151–153 | | H | H | H | |
| 364 | | M − H 361 | H | H | H | |

TABLE 2-continued
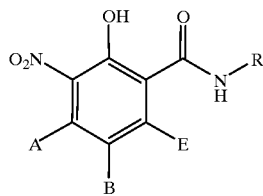
Note: Left most bond on R indicates linking bond to NH in structure above.
| Compound Number | Melting Point (° C.) | Molecular Ion (M) | A | B | E | R |
|---|---|---|---|---|---|---|
| 365 | | M − H 395 | H | H | H | |
| 366 | 120–122 | | H | H | H | |
| 367 | | | H | H | H | |
| 368 | | | H | H | H | |
| 369 | 103–105 | | H | H | H | |
| 370 | | 376 | H | H | H | |

TABLE 2-continued
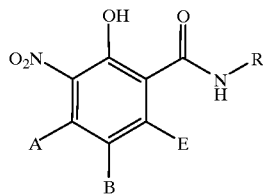
Note: Left most bond on R indicates linking bond to NH in structure above.
| Compound Number | Melting Point (° C.) | Molecular Ion (M) | A | B | E | R |
|---|---|---|---|---|---|---|
| 371 | | 382 | H | H | H | |
| 372 | 118–121 | | H | H | H | |
| 373 | 112–114 | | H | H | H | |
| 374 | 182–184 | 336 | H | H | OH | |
| 375 | | M + H 265 | H | H | H | |
| 376 | | M + H 279 | H | H | H | |

TABLE 2-continued
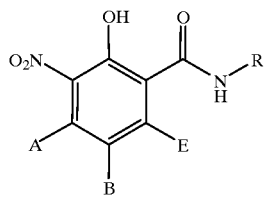
Note: Left most bond on R indicates linking bond to NH in structure above.
| Compound Number | Melting Point (° C.) | Molecular Ion (M) | A | B | E | R |
|---|---|---|---|---|---|---|
| 377 | | | H | H | H | |
| 378 | | M − H 343 | H | H | H | |
| 379 | | 292 | H | H | H | |
| 380 | | 332 | H | H | H | |
| 381 | | 326 | H | H | H | |
| 382 | 54–57 | M + H 321 | H | H | H | |

TABLE 2-continued
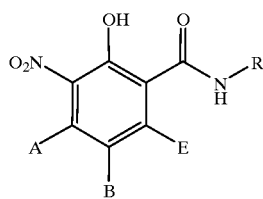
Note: Left most bond on R indicates linking bond to NH in structure above.
| Compound Number | Melting Point (° C.) | Molecular Ion (M) | A | B | E | R |
|---|---|---|---|---|---|---|
| 383 | | 332 | H | H | H | |
| 384 | 97–100 | M + H 265 | H | H | H | |
| 387 | | 279 | H | H | H | |
| 388 | 144–146 | 334 | H | H | H | |
| 389 | | 292 | H | H | H | |
| 390 | | 292 | H | H | H | |
| 391 | | 306 | H | H | H | |
| 392 | | | H | H | H | |

TABLE 2-continued
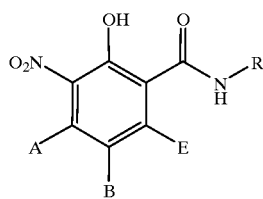
Note: Left most bond on R indicates linking bond to NH in structure above.
| Compound Number | Melting Point (° C.) | Molecular Ion (M) | A | B | E | R |
|---|---|---|---|---|---|---|
| 393 | 139–141 | | H | H | H | |
| 394 | 168–170 | | H | H | H | |
| 395 | 108–110 | 397, 399 | H | Br | H | |
| 396 | 110–112 | 338 | H | F | H | |
| 397 | | 292 | H | H | H | |
| 398 | | M − H 409 | H | H | H | |

TABLE 2-continued
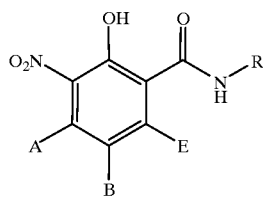
Note: Left most bond on R indicates linking bond to NH in structure above.
| Compound Number | Melting Point (° C.) | Molecular Ion (M) | A | B | E | R |
|---|---|---|---|---|---|---|
| 399 | 208–210 | 365 | H | NO$_2$ | H | |
| 400 | | | H | H | H | |
| 401 | | | H | H | H | |
| 402 | 136–138 | | H | H | H | |
| 403 | | | H | H | H | |
| 404 | | | H | H | H | |

TABLE 2-continued
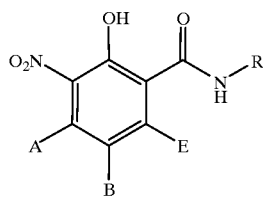
Note: Left most bond on R indicates linking bond to NH in structure above.
| Compound Number | Melting Point (° C.) | Molecular Ion (M) | A | B | E | R |
|---|---|---|---|---|---|---|
| 405 | 159–160 | M − H 335 | H | H | H | |
| 406 | 155–156 | M − H 335 | H | H | H | |
| 407 | | M − H 387 | H | H | H | |
| 408 | | M − H 429 | H | H | H | |
| 409 | | | H | H | H | |
| 410 | | 293 | H | H | H | |

TABLE 2-continued
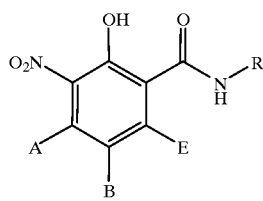
Note: Left most bond on R indicates linking bond to NH in structure above.
| Compound Number | Melting Point (° C.) | Molecular Ion (M) | A | B | E | R |
|---|---|---|---|---|---|---|
| 411 | | | H | H | H | |
| 412 | | M − H 393 | H | H | H | |
| 413 | | | H | H | H | |
| 414 | | | H | H | H | |
| 415 | | 306 | H | H | H | |
| 416 | | | H | H | H | |
| 417 | | 278 | H | H | H | |

TABLE 2-continued
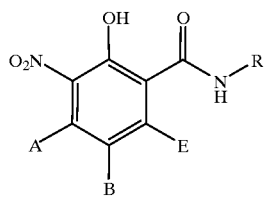
Note: Left most bond on R indicates linking bond to NH in structure above.
| Compound Number | Melting Point (° C.) | Molecular Ion (M) | A | B | E | R |
|---|---|---|---|---|---|---|
| 418 | 136–140 | M + H 307 | H | H | H | |
| 419 | 163–165 | M − H 347 | H | H | H | |
| 420 | 151–154 | | H | H | H | |
| 421 | | | H | H | H | |
| 422 | | | H | H | H | |
| 423 | | 368 | H | H | H | |

TABLE 2-continued
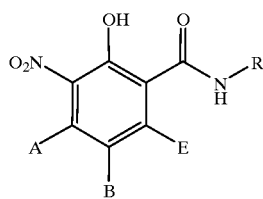
Note: Left most bond on R indicates linking bond to NH in structure above.
| Compound Number | Melting Point (° C.) | Molecular Ion (M) | A | B | E | R |
|---|---|---|---|---|---|---|
| 424 | | M + H 375 | H | H | H | |
| 425 | | | H | H | H | |
| 426 | 134–135 | M + H 335 | H | H | H | |
| 427 | | | H | H | H | |
| 428 | | | H | H | H | |
| 429 | 71–78 | M + H 365 | H | F | H | |

TABLE 2-continued
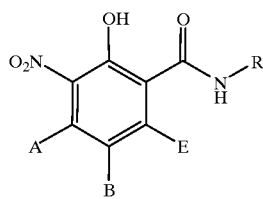
Note: Left most bond on R indicates linking bond to NH in structure above.
| Compound Number | Melting Point (° C.) | Molecular Ion (M) | A | B | E | R |
|---|---|---|---|---|---|---|
| 430 | | 306 | H | H | H | |
| 431 | | 340 | H | H | H | |
| 432 | | | H | H | H | |
| 433 | 149–154 | M − H 347 | H | H | H | |
| 434 | | | H | H | H | |
| 435 | 88–90 | M − H 404 | H | H | H | |

TABLE 2-continued
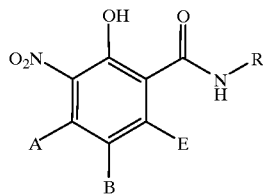
Note: Left most bond on R indicates linking bond to NH in structure above.
| Compound Number | Melting Point (° C.) | Molecular Ion (M) | A | B | E | R |
|---|---|---|---|---|---|---|
| 436 | | | H | H | H | |
| 437 | | | H | H | H | |
| 438 | | | H | F | H | |
| 439 | 105–108 | M − H 345 | H | H | H | |
| 440 | | | H | H | H | |
| 441 | | | H | H | H | |

TABLE 2-continued
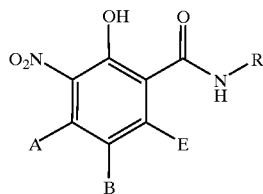
Note: Left most bond on R indicates linking bond to NH in structure above.
| Compound Number | Melting Point (° C.) | Molecular Ion (M) | A | B | E | R |
|---|---|---|---|---|---|---|
| 442 | 133–137 | | H | H | H | |
| 443 | | | H | H | H | |
| 444 | | | H | H | H | |
| 445 | | | H | H | H | |
| 446 | | | H | H | H | |
| 447 | 133–135 | | H | H | H | |

TABLE 2-continued
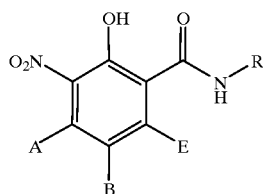
Note: Left most bond on R indicates linking bond to NH in structure above.
| Compound Number | Melting Point (° C.) | Molecular Ion (M) | A | B | E | R |
|---|---|---|---|---|---|---|
| 448 | | | H | H | H | |
| 449 | | | H | H | H | |
| 450 | | M − H 347 | H | H | H | |
| 451 | | | F | H | H | |
| 452 | 224–226 | 392 | H | NHCONHCH$_3$ | H | |
| 453 | | | H | H | H | |

TABLE 2-continued
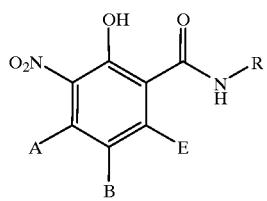
Note: Left most bond on R indicates linking bond to NH in structure above.
| Compound Number | Melting Point (° C.) | Molecular Ion (M) | A | B | E | R |
|---|---|---|---|---|---|---|
| 454 | | M + H 349 | H | H | H | |
| 455 | | | H | H | H | |
| 456 | | | H | H | H | |
| 457 | | | H | H | H | |
| 458 | | | H | H | H | |
| 459 | 137–139 | M − H 353 | H | H | H | |

TABLE 2-continued
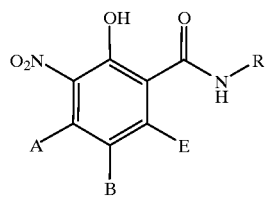
Note: Left most bond on R indicates linking bond to NH in structure above.
| Compound Number | Melting Point (° C.) | Molecular Ion (M) | A | B | E | R |
|---|---|---|---|---|---|---|
| 460 | | | H | H | H | |
| 461 | 168–170 | | H | H | H | |
| 462 | 137–139 | M − H 331 | H | H | H | |
| 463 | | | H | H | H | |
| 464 | 117–121 | M − H 303 | H | H | H | |
| 465 | | | H | H | H | |

TABLE 2-continued

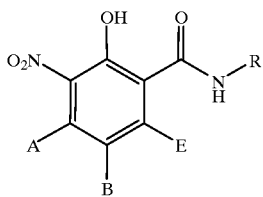

Note: Left most bond on R indicates linking bond to NH in structure above.

| Compound Number | Melting Point (° C.) | Molecular Ion (M) | A | B | E | R |
|---|---|---|---|---|---|---|
| 466 | 189–192 | | H | H | OCH₃ | |
| 467 | 159–161 | M + H 355 | H | H | Cl | |
| 468 | 120–122 | 349 | H | H | NHCH₃ | |
| 469 | 211–214 | 366 | H | H | SCH₃ | |
| 470 | | 393 | H | H | H | |

The foregoing examples demonstrate the preparation of a variety of 3-nitrosalicylamides. Among the preferred compounds are those in which A is hydrogen, B is selected from the group consisting of F, H, Cl and fonnamido, and E is selected from the group consisting of OH, F and H.

Preparing the AASA Compound 6

Preparation of 3-Formamido-2-hydroxy-N-(3-ethyl-3,5,5-trimethylcyclohexyl)-benzamide To a solution of N-(3-ethyl-3,5,5-trimethylcyclohexyl)-2-hydroxy-3-nitrobenzamide (3.60 g) in ethyl acetate (75 ml) was added 5% Pd/C (0.40 g) catalyst. The resulting mixture was subjected to a hydrogen atmosphere (initial H₂ pressure=50 psi) using a Parr shaker apparatus. When hydrogen uptake ceased (approximately 30 minutes), the hydrogen atmosphere was purged. A stir bar was added to the reaction bottle and to the stirred reaction mixture acetic-formic anhydride (3 ml) was added all at once. After stirring at room temperature for 30 minutes, the reaction was filtered, washed with saturated sodium bicarbonate solution (100 ml). then with a saturated sodium chloride solution (100 ml), dried (MgSO₄) and the solvent evaporated to give the desired product as a white solid foam (3.5 g). An analytical sample could be prepared by recrystallization from a methanol/water mixture to give an off-white crystalline solid (m.p.=166–168° C.). $^{13}$C NMR (CDCl$_3$) showed this material to be approximately a 6:4 mixture of diastereomers.

Preparation of 5-Chloro-3-formamido-2-hydroxy-N-(3,3,5,5-tetramethylcyclohexyl)-benzamide 0.75 g of the nitroamide (4,X=5–Cl) and 0.2 g of 5% platinum on sulfided carbon in 100 ml of ethyl acetate was hydrogenated at 40 lbs/sq. in. hydrogen pressure on a Parr shaker apparatus. This mixture was diluted to 125 ml with extra ethyl acetate and was treated as quickly as possible with 2 ml of acetic-formic anhydride. The mixture was stirred overnight at room temperature and then filtered to remove the hydrogenation catalyst. ihe filtrate was washed with 150 ml portions of 50% saturated sodium bicarbonate, water. and saturated sodium chloride solution and then dried over magnesium sulfate. The dried solution was filtered and stripped. The crude solid was recrystallized from methylene chloridecyclohexane to give the product as 0.44 g of light tan crystals (m.p. 214–15°). Mass spectrum—M/Z 352.

Based upon the foregoing. the following acylated aminosalicylanides listed in Table 3 were prepared. In each instance. Y=O. However, analogous compounds with Y=S. NOH, NH or NOC$_{1-3}$ alkyl may be prepared from the corresponding 3-nitrosalicylamides by the methods discussed below.

Intermediate nitro amides 6 may be converted to thioamides (Y=S) by reaction with phosphorus pentasulfide or Lawesson's reagent (Perregaard, J.; Thomsen, I.; Lawesson, S.—O.; Bull Soc Chim Belg 1977, 86) in an inert solvent at elevated temperature. These thioamides may be carried on to final acylaminosalicylthioamides by a variety of known methods. The above nitro thioamides may also be reacted with anmonia, hydroxylarnine, or O—alkylhydroxylamines by methods such as shown in Sankyo KK. Japan Patent, 3144570. p.08772B-C, 1979 and Deodhar. K. D.; D'Sa, A. D.; Pednekar, S. R.; Kanekar, D. S. Synthesis 1982, 853 to form nitro amidines (Y=NH) or amidoximes (Y=NOH or NOR). which can be carried on to the final products by a variety of known methods.

TABLE 3

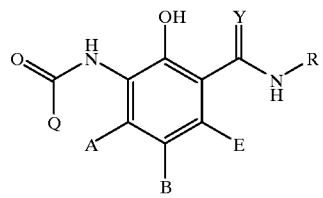

Note: Left most bond on R indicates linking bond to NH in structure above

| Compound Number | Melting Point (° C.) | Molecular Ion (M) | Q | A | B | E | R |
|---|---|---|---|---|---|---|---|
| 501 | 185–190 | M + H 317 | H | H | H | H | |
| 502 | 171–180 | M − H 337 | H | H | H | H | |
| 503 | 104–108 | M + H 339 | H | H | H | H | |
| 504 | 162–165 | M + H 319 | H | H | H | H | |

TABLE 3-continued
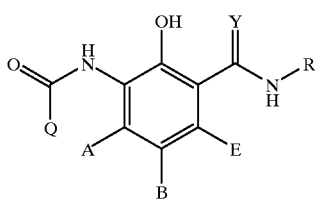
Note: Left most bond on R indicates linking bond to NH in structure above
| Compound Number | Melting Point (° C.) | Molecular Ion (M) | Q | A | B | E | R |
|---|---|---|---|---|---|---|---|
| 505 | 145–150 | | H | H | H | H | |
| 506 | | M + H 347 | NHCH₃ | H | H | H | |
| 507 | 196–199 | M + H 332 | CH₃ | H | H | H | |
| 508 | | 362 | H | H | H | H | |
| 509 | 214–215 | 352 | H | H | Cl | H | |
| 510 | 175–177 | | H | H | H | H | |
| 511 | 140–144 | 346 | H | H | H | H | |

TABLE 3-continued
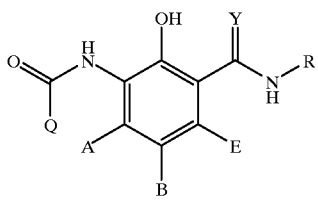
Note: Left most bond on R indicates linking bond to NH in structure above
| Compound Number | Melting Point (° C.) | Molecular Ion (M) | Q | A | B | E | R |
|---|---|---|---|---|---|---|---|
| 512 | | 332 | H | H | H | H | |
| 513 | | M − H 359 | H | H | H | H | |
| 514 | | 344 | H | H | H | H | |
| 515 | | 380 | H | H | H | H | |
| 516 | | 304 | H | H | H | H | |
| 517 | | 332 | H | H | H | H | |

TABLE 3-continued
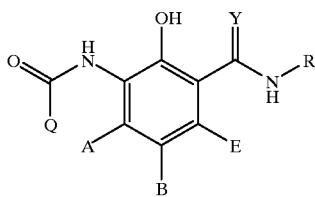
Note: Left most bond on R indicates linking bond to NH in structure above
| Compound Number | Melting Point (° C.) | Molecular Ion (M) | Q | A | B | E | R |
|---|---|---|---|---|---|---|---|
| 518 | | 398 | H | H | H | H | |
| 519 | | 360 | H | H | H | H | |
| 520 | 132–134 | | H | H | H | H | |
| 521 | 154–157 | | H | H | H | H | |
| 522 | | 346 | H | H | H | H | |
| 523 | | 344 | H | H | H | H | |

TABLE 3-continued
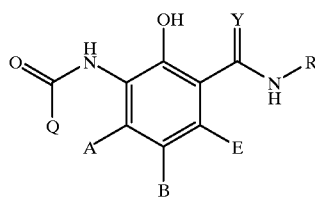
Note: Left most bond on R indicates linking bond to NH in structure above
| Compound Number | Melting Point (° C.) | Molecular Ion (M) | Q | A | B | E | R |
|---|---|---|---|---|---|---|---|
| 524 | | M + H 333 | H | H | H | H | |
| 525 | 187–189 | | H | H | H | H | |
| 526 | 219–221 | | H | H | H | H | |
| 527 | | 410 | H | H | H | H | |
| 528 | | 330 | H | H | H | H | |
| 529 | 141–145 | | H | H | H | H | |

TABLE 3-continued
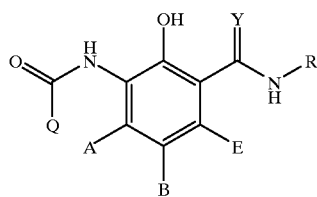
Note: Left most bond on R indicates linking bond to NH in structure above
| Compound Number | Melting Point (° C.) | Molecular Ion (M) | Q | A | B | E | R |
|---|---|---|---|---|---|---|---|
| 530 | | 348 | H | H | H | H | |
| 531 | | 348 | H | H | H | H | |
| 532 | | M − H 373 | H | H | H | H | |
| 533 | | M − H 317 | H | H | H | H | |
| 534 | | M − H 317 | H | H | H | H | |
| 535 | 114–117 | | H | H | H | H | |

TABLE 3-continued
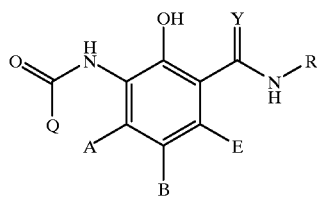
Note: Left most bond on R indicates linking bond to NH in structure above
| Compound Number | Melting Point (° C.) | Molecular Ion (M) | Q | A | B | E | R |
|---|---|---|---|---|---|---|---|
| 536 | 100–103 | | H | H | H | H | |
| 537 | | | H | H | H | H | |
| 538 | | 352 | H | H | H | H | |
| 539 | | 352 | H | H | H | H | |
| 540 | | M − H 359 | H | H | H | H | |

TABLE 3-continued
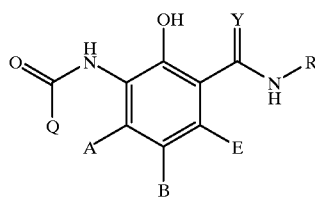
Note: Left most bond on R indicates linking bond to NH in structure above
| Compound Number | Melting Point (° C.) | Molecular Ion (M) | Q | A | B | E | R |
|---|---|---|---|---|---|---|---|
| 541 | | 360 | H | H | H | H | |
| 542 | 168–171 | | | H | H H | H | |
| 543 | 149–152 | | | H | H H | H | |
| 544 | 172–173 | | | H | H H | H | |
| 545 | | 410 | H | H | H | H | |
| 546 | | 429 | H | H | H | H | |

TABLE 3-continued
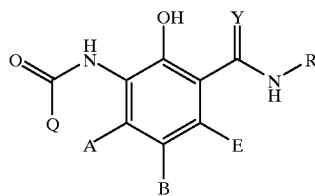
Note: Left most bond on R indicates linking bond to NH in structure above
| Compound Number | Melting Point (° C.) | Molecular Ion (M) | Q | A | B | E | R |
|---|---|---|---|---|---|---|---|
| 547 | | 366 | H | H | H | H | |
| 548 | | M + H 354 | H | H | H | H | |
| 549 | | 353 | H | H | H | H | |
| 550 | 95 | 394 | H | H | H | H | |
| 551 | | M + H 376 | H | H | H | H | |

TABLE 3-continued
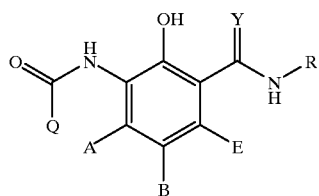
Note: Left most bond on R indicates linking bond to NH in structure above
| Compound Number | Melting Point (° C.) | Molecular Ion (M) | Q | A | B | E | R |
|---|---|---|---|---|---|---|---|
| 552 | | M − H 436 | H | H | H | H | |
| 553 | | 332 | H | H | H | H | |
| 554 | | 332 | H | H | H | H | |
| 555 | | M − H 495 | H | H | H | H | |
| 556 | | M − H 393 | H | H | H | H | |

TABLE 3-continued
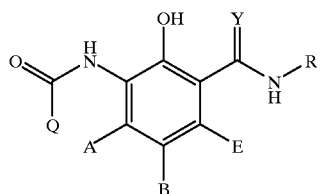
Note: Left most bond on R indicates linking bond to NH in structure above
| Compound Number | Melting Point (° C.) | Molecular Ion (M) | Q | A | B | E | R |
|---|---|---|---|---|---|---|---|
| 557 | | M − H 345 | H | H | H | H | |
| 558 | | 380 | H | H | H | H | |
| 559 | | M − H 409 | H | H | H | H | |
| 560 | | M − H 409 | H | H | H | H | |
| 561 | | 403 | H | H | H | H | |

TABLE 3-continued
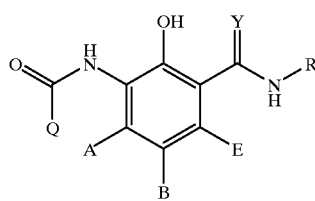
Note: Left most bond on R indicates linking bond to NH in structure above
| Compound Number | Melting Point (° C.) | Molecular Ion (M) | Q | A | B | E | R |
|---|---|---|---|---|---|---|---|
| 562 | | 346 | H | H | H | H | 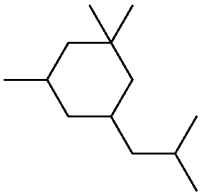 |
| 563 | | M − H 345 | H | H | H | H | 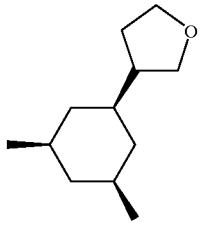 |
| 564 | | M − H 317 | H | H | H | H | 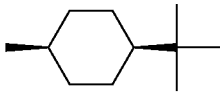 |
| 565 | 169–171 | | H | H | H | H | 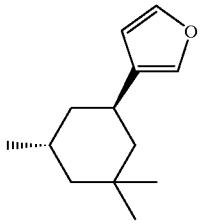 |
| 566 | | M − H 355 | H | H | H | H | 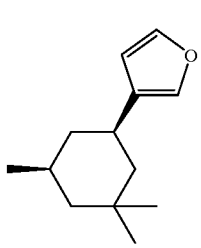 |
| 567 | | M + H 361 | H | H | H | H | 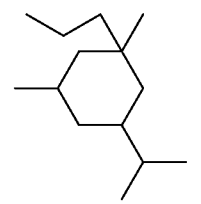 |

TABLE 3-continued
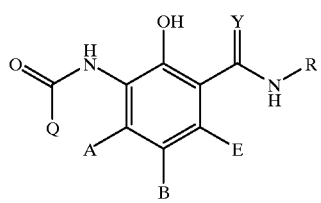
Note: Left most bond on R indicates linking bond to NH in structure above
| Compound Number | Melting Point (° C.) | Molecular Ion (M) | Q | A | B | E | R |
|---|---|---|---|---|---|---|---|
| 568 | | M + H 395 | H | H | H | H | 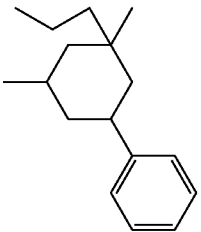 |
| 569 | 175–181 | | H | H | H | H | 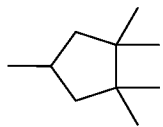 |
| 570 | | 346 | H | H | H | H | 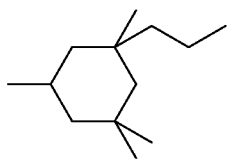 |
| 571 | | 318 | H | H | H | H | 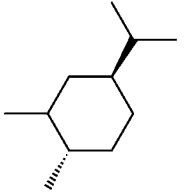 |
| 572 | 179–180 | | H | H | H | H | 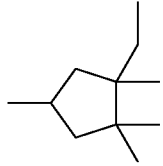 |
| 573 | | 374 | H | H | H | H | 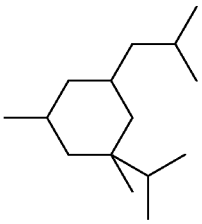 |

TABLE 3-continued
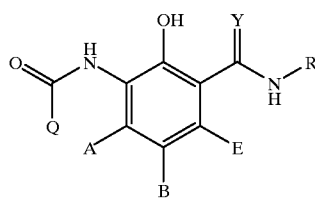
Note: Left most bond on R indicates linking bond to NH in structure above
| Compound Number | Melting Point (° C.) | Molecular Ion (M) | Q | A | B | E | R |
|---|---|---|---|---|---|---|---|
| 574 | | 380 | H | H | H | H | |
| 575 | | M − H 355 | H | H | H | H | |
| 576 | | M − H 355 | H | H | H | H | |
| 577 | | | H | H | H | OH | |
| 578 | | M − H 261 | H | H | H | H | |
| 579 | | 276 | H | H | H | H | |

TABLE 3-continued
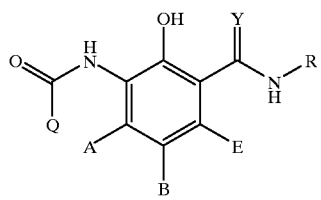
Note: Left most bond on R indicates linking bond to NH in structure above
| Compound Number | Melting Point (° C.) | Molecular Ion (M) | Q | A | B | E | R |
|---|---|---|---|---|---|---|---|
| 580 | | 332 | H | H | H | H | 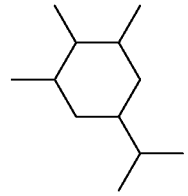 |
| 581 | | 342 | H | H | H | H | 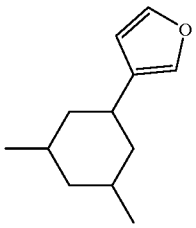 |
| 582 | | M + H 291 | H | H | H | H | 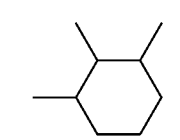 |
| 583 | | 330 | H | H | H | H | 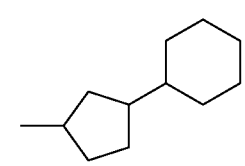 |
| 584 | | 324 | H | H | H | H | 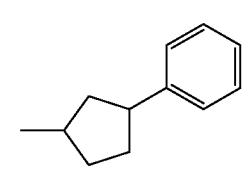 |
| 585 | | 318 | H | H | H | H | 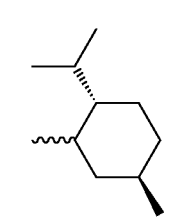 |

TABLE 3-continued
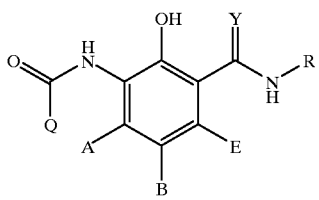
Note: Left most bond on R indicates linking bond to NH in structure above
| Compound Number | Melting Point (° C.) | Molecular Ion (M) | Q | A | B | E | R |
|---|---|---|---|---|---|---|---|
| 586 | | 330 | H | H | H | H | 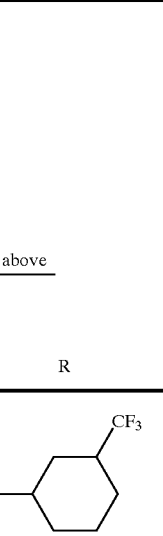 |
| 587 | | 262 | H | H | H | H | 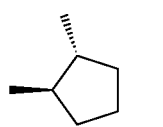 |
| 588 | | 262 | H | H | H | H | 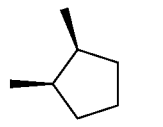 |
| 589 | | 276 | H | H | H | H | 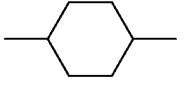 |
| 590 | 134–136 | 332 | H | H | H | H | 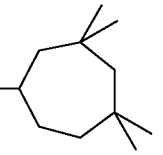 |
| 591 | | 290 | H | H | H | H | 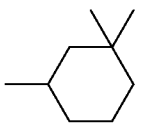 |
| 592 | | 290 | H | H | H | H | 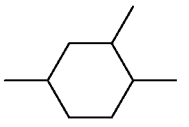 |
| 593 | | 304 | H | H | H | H | 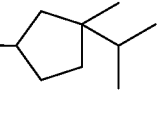 |

TABLE 3-continued
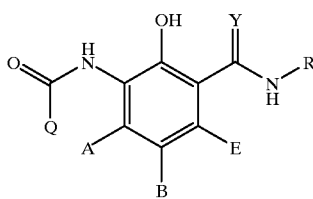
Note: Left most bond on R indicates linking bond to NH in structure above
| Compound Number | Melting Point (° C.) | Molecular Ion (M) | Q | A | B | E | R |
|---|---|---|---|---|---|---|---|
| 594 | | 440 | H | H | H | H | |
| 595 | | M + H 425 | H | H | H | H | |
| 596 | | 424 | H | H | H | H | |
| 597 | 210–212 | 396, 398 | H | H | Br | H | |
| 598 | 175–178 | 336 | H | H | F | H | |

TABLE 3-continued
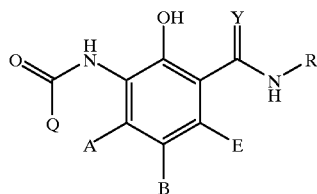
Note: Left most bond on R indicates linking bond to NH in structure above
| Compound Number | Melting Point (° C.) | Molecular Ion (M) | Q | A | B | E | R |
|---|---|---|---|---|---|---|---|
| 599 | | 290 | H | H | H | H | |
| 600 | 233–237 | M + H 362 | H | H | NHCHO | H | |
| 601 | 170–173 | 346 | CH$_2$CH$_3$ | H | H | H | |
| 602 | | M − H 407 | H | H | H | H | |
| 603 | 228–233 | 364 | H | H | NO$_2$ | H | |
| 604 | | M − H 317 | H | H | H | H | |

TABLE 3-continued
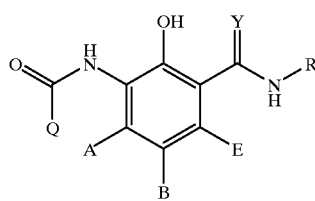
Note: Left most bond on R indicates linking bond to NH in structure above
| Compound Number | Melting Point (° C.) | Molecular Ion (M) | Q | A | B | E | R |
|---|---|---|---|---|---|---|---|
| 605 | | M − H 331 | H | H | H | H | 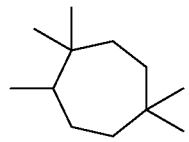 |
| 606 | | M − H 331 | H | H | H | H | 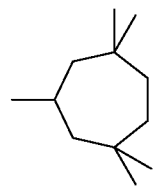 |
| 607 | | 358 | H | H | H | H | 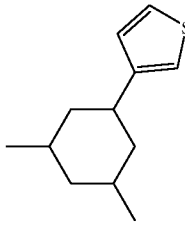 |
| 608 | | 451 | H | H | H | H | 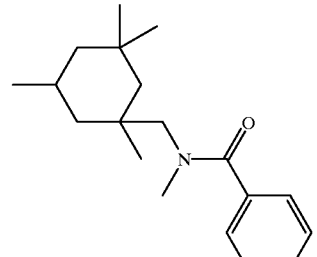 |
| 609 | | M − H 360 | N(CH$_3$)$_2$ | H | H | H | 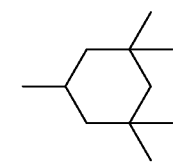 |
| 610 | 194–195 | M + H 335 | H | H | H | H | 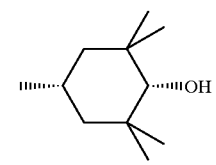 |

TABLE 3-continued
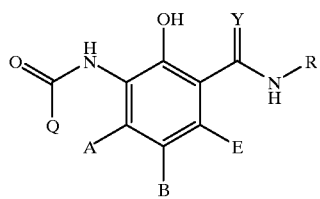
Note: Left most bond on R indicates linking bond to NH in structure above
| Compound Number | Melting Point (° C.) | Molecular Ion (M) | Q | A | B | E | R |
|---|---|---|---|---|---|---|---|
| 611 | 244–245 | M + H 335 | H | H | H | H | |
| 612 | | M + H 387 | H | H | H | H | |
| 613 | | M − H 427 | H | H | H | H | |
| 614 | 251–253 | M − H 409 | H | H | H | H | |
| 615 | 80–82 | 290 | H | H | H | H | |

TABLE 3-continued
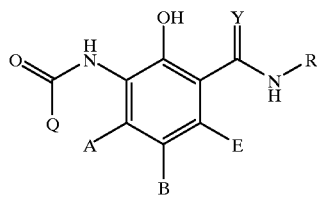
Note: Left most bond on R indicates linking bond to NH in structure above
| Compound Number | Melting Point (° C.) | Molecular Ion (M) | Q | A | B | E | R |
|---|---|---|---|---|---|---|---|
| 616 | | M + H 363 | H | H | H | H | |
| 617 | 165–167 | | H | H | H | H | |
| 618 | | | H | H | H | H | |
| 619 | | | H | H | H | H | |
| 620 | | 304 | H | H | H | H | |
| 621 | | | H | H | H | H | |

TABLE 3-continued
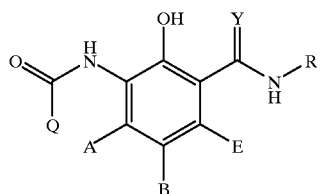
Note: Left most bond on R indicates linking bond to NH in structure above
| Compound Number | Melting Point (° C.) | Molecular Ion (M) | Q | A | B | E | R |
|---|---|---|---|---|---|---|---|
| 622 | | 376 | H | H | H | H | |
| 623 | | 304 | H | H | H | H | |
| 624 | 171–173 | 346 | H | H | H | H | |
| 625 | 164–166 | | H | H | H | H | |
| 626 | | | H | H | H | H | |
| 627 | 165–167 | | H | H | H | H | |

TABLE 3-continued
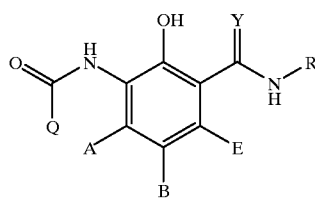
Note: Left most bond on R indicates linking bond to NH in structure above
| Compound Number | Melting Point (° C.) | Molecular Ion (M) | Q | A | B | E | R |
|---|---|---|---|---|---|---|---|
| 628 | | 366 | H | H | H | H | |
| 629 | | 372 | H | H | H | H | |
| 630 | | | H | H | H | H | |
| 631 | | 332 | H | H | H | H | |
| 632 | 149–150 | 424 | H | H | H | H | |
| 633 | 123–124 | 348 | H | H | H | H | |

TABLE 3-continued
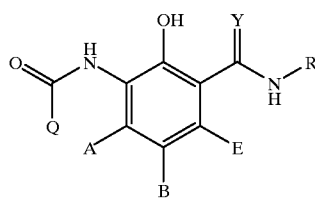
Note: Left most bond on R indicates linking bond to NH in structure above
| Compound Number | Melting Point (° C.) | Molecular Ion (M) | Q | A | B | E | R |
|---|---|---|---|---|---|---|---|
| 634 | | 362 | H | H | F | H | |
| 635 | | 304 | H | H | H | H | |
| 636 | | 338 | H | H | H | H | |
| 637 | | 319 | H | H | H | H | |
| 638 | 151–153 | M − H 345 | H | H | H | H | |
| 639 | | M − H 345 | H | H | H | H | |

TABLE 3-continued
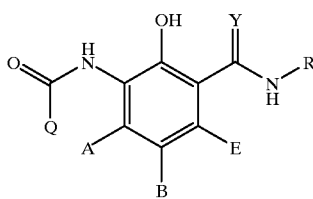
Note: Left most bond on R indicates linking bond to NH in structure above
| Compound Number | Melting Point (° C.) | Molecular Ion (M) | Q | A | B | E | R |
|---|---|---|---|---|---|---|---|
| 640 | 121–122 | M − H 403 | H | H | H | H | |
| 641 | 156–157 | M − H 403 | H | H | H | H | |
| 642 | | M − H 407 | H | H | H | H | |
| 643 | | M − H 391 | H | H | H | H | |
| 644 | | 350 | H | H | F | H | |
| 645 | | M − H 345 | H | H | H | H | |

TABLE 3-continued
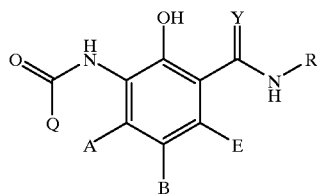
Note: Left most bond on R indicates linking bond to NH in structure above
| Compound Number | Melting Point (° C.) | Molecular Ion (M) | Q | A | B | E | R |
|---|---|---|---|---|---|---|---|
| 646 | 212–214 | 350 | CH₃ | H | F | H | |
| 647 | | M − H 345 | H | H | H | H | |
| 648 | | M − H 345 | H | H | H | H | |
| 649 | | M − H 361 | H | H | H | H | |
| 650 | | | H | H | H | H | |
| 651 | | | H | H | H | H | |

TABLE 3-continued
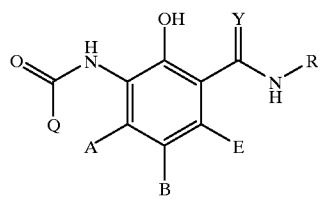
Note: Left most bond on R indicates linking bond to NH in structure above
| Compound Number | Melting Point (° C.) | Molecular Ion (M) | Q | A | B | E | R |
|---|---|---|---|---|---|---|---|
| 652 | | | H | H | H | H | 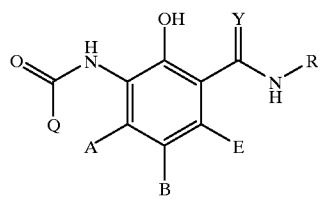 |
| 653 | | M − H 391 | H | H | H | H | 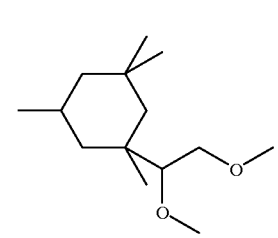 |
| 654 | | M − H 317 | H | H | H | H | 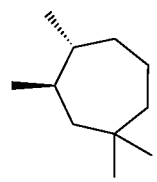 |
| 655 | | | H | H | H | H | 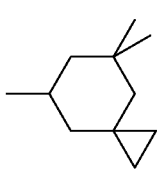 |
| 656 | | | H | H | H | H | 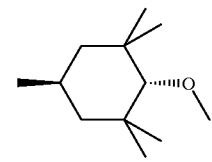 |
| 657 | 140–160 | M − H 345 | H | H | H | H | 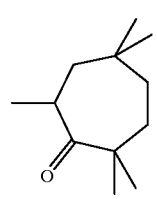 |

TABLE 3-continued
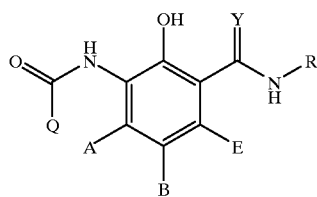
Note: Left most bond on R indicates linking bond to NH in structure above
| Compound Number | Melting Point (° C.) | Molecular Ion (M) | Q | A | B | E | R |
|---|---|---|---|---|---|---|---|
| 658 | 232–240 | M − H 335 | H | F | H | H | |
| 659 | | 390 | H | H | NHCONH CH₃ | H | |
| 660 | | M + H 349 | H | H | H | H | |
| 661 | | 346 | H | H | H | H | |
| 662 | | 451 | H | H | H | H | |
| 663 | | 376 | H | H | H | H | |

TABLE 3-continued
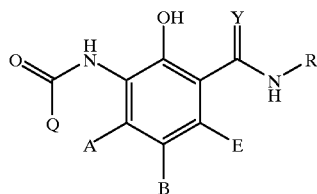
Note: Left most bond on R indicates linking bond to NH in structure above
| Compound Number | Melting Point (° C.) | Molecular Ion (M) | Q | A | B | E | R |
|---|---|---|---|---|---|---|---|
| 664 | | M − H 329 | H | H | H | H | |
| 665 | | M − H 329 | H | H | H | H | |
| 666 | | M − H 351 | H | H | H | H | |
| 667 | 127–130 | | H | H | H | H | |
| 668 | 171–173 | M − H 313 | H | H | H | H | |
| 669 | 230–236 | 333 | $NH_2$ | H | H | H | |

TABLE 3-continued
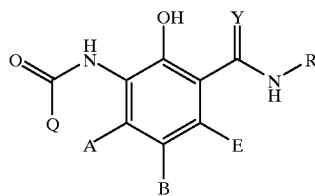
Note: Left most bond on R indicates linking bond to NH in structure above
| Compound Number | Melting Point (° C.) | Molecular Ion (M) | Q | A | B | E | R |
|---|---|---|---|---|---|---|---|
| 670 | | M − H 329 | H | H | H | H | |
| 671 | | 332 | H | H | H | H | |
| 672 | | M − H 301 | H | H | H | H | |
| 673 | | M − H 317 | H | H | H | H | |
| 674 | 151–154 | 348 | H | H | H | OCH$_3$ | |
| 675 | 170–173 | 353 | H | H | H | Cl | |

TABLE 3-continued

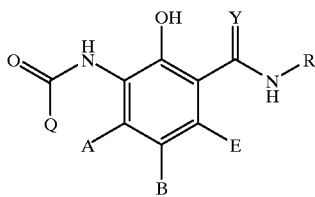

Note: Left most bond on R indicates linking bond to NH in structure above

| Compound Number | Melting Point (° C.) | Molecular Ion (M) | Q | A | B | E | R |
|---|---|---|---|---|---|---|---|
| 676 | 174–180 | 376 | H | H | H | N(CH$_3$)CHO | |
| 677 | 105–107 | 364 | H | H | H | SCH$_3$ | |
| 678 | | 390 | H | H | H | H | |

The following compounds follow the above format, except that Y is NH in compound 679 and is NOCH$_3$ in compound 680.

| | | | | | | | |
|---|---|---|---|---|---|---|---|
| 679 | | 317 | H | H | H | H | |
| 680 | 82–92 | M − H 374 | H | H | H | H | |

Fungicide Utility

The compounds of the present invention have been found to control fungi, particularly plant pathogens. When employed in the treatment of plant fungal diseases, the compounds are applied to the plants in a disease inhibiting and phytologically acceptable amount. Application may be performed before and/or after the infection with fungi on plants. Application may also be made through treatment of seeds of plants, soil where plants grow, paddy fields for seedlings, or water for perfusion. The compounds of the invention may also be used to protect stored grain, wood products and other non-plant loci from fungal infestation The AASA compounds of Formula I show strong fingicidal activity against a wide variety of ftmgi. The following tests were performed in the laboratory and illustrate the fungicidal efficacy of the compounds of the invention. The following protocols are established and understood by those in the art as evidencing the utility of the compounds for the purposes indicated.

Compound formulation was accomplished by dissolving technical materials in acetone, with serial dilutions then made in acetone to obtain desired concentrations. Final treatment volumes were obtained by adding nine volumes 0.05% aqueous Tween-20 or 0.01% Triton X-100, depending upon the pathogen.

Downy Mildew of Grape (*Plasmopara viticola*-PLASVI) (24 Hour Protectant): Vines (cultivar Carignane) were grown from seed in a soilless peat based potting mixture ("Metromix") until the seedlings were 10–20 cm tall. These plants were then sprayed to run off with the test compound at a rate of 100 ppm. After 24 hours the test plants were inoculated by spraying with an aqueous sporangia suspension of *Plasmopara viticola*. The plants were then transferred to the greenhouse until disease developed on the untreated control plants.

Downy Mildew of Grape (*Plasmopara viticola*-PLASVI) (24 Hour Curative): Vines (culTivar Carigrane) were grown from seed in a soilless peat-based potting mixture ("Metromix") until the seedlings were 10–20cm tall. The test plants were inoculated by spraying with an aqueous sporangia suspension of *Plasmopara viticola*. After 24 hours these plants were then sprayed to run off with the test compound at a rate of 100 ppm. The plants were then transferred to the greenhouse until disease developed on the untreated control plants.

Late Blight of Tomato (*Phytophthora infestans*-PHYTIN): Tomatoes (cultivar Rutgers) were grown from seed in a soilless peat-based potting mixture ("Metromix") until the seedlings were 10–20 cm tall. These plants were then sprayed to run off with the test compound at a rate of 100 ppm. After 24 hours the test plants were inoculated by spraying with an aqueous sporangia suspension of *Phytophthora infestans*. The plants were then transferred to the greenhouse until disease developed on the untreated control plants.

Apple Scab (*Venturia inaequalis*-VENTIN): Apples (cultivar Red Delicious) were grown from seed in a soil-less peat-based potting mixture ("Metromix") until the seedlings were 10–20 cm tall. These plants were then sprayed to run off with the test compound at a rate of 100 ppm After 48 hours the test plants were inoculated by spraying with an aqueous suspension of *Venturia inaequalis* spores. The plants were then transferred to the greenhouse until disease developed on the untreated control plants.

Brown rust of Wheat (*Puccinia recondita*-PUCCRT): Wheat (cultivar Monon) was grown in a soilless peat-based potting mixture ("Metromix") until the seedlings were 10–20 cm tall. These plants were then sprayed to run off with the test compound at a rate of 100 ppm. After 24 hours the test plants were inoculated by spraying with an aqueous spore suspension of *Puccinia recondita*. The plants were then transferred to the greenhouse until disease developed on the untreated control plants.

Rice Blast (*Pyricularia oryzae*-PYRIOR): Rice (cultivar M9) was grown from seed in a soilless peat-based potting mixture ("Metromix") until the seedlings were 10–20 cm tall. These plants were then sprayed to run off with the test compound at a rate of i 100 ppm. After 24 hours the test plants were inoculated by spraying with an aqueous suspension of *Pyricularia oryzae*conidia. The plants were then transferred to the greenhouse until disease developed on the untreated control plants.

Cercospora Leaf Spot of Beet (*Cercospora beticola*-CERCBE): Sugar beet (cultivar Interstate) was grown in a soilless peat-based potting mixture ("Metromix") until the seedlings were 10–20 cm tall. These plants were then sprayed to run off with the test compound at a rate of 100 ppm. After 24 hours the test plants were inoculated by spraying with an aqueous spore suspension of *Cercospora beticola*. The plants were then transferred to the greenhouse until disease developed on the untreated control plants.

Powdery Mildew of Wheat (*Erysiphe graminis*-ERYSGT): Wheat (cultivar Mtonon) was grown in a soilless peat-based potting mixture ("Metromix") until the seedlings were 10–20 cm tall. These plants were then inoculated with *Erysiphe graminis* by dusting spores from stock plants onto the test plants. After 24 hours the plants were sprayed to run off with the test compound at a rate of 100 ppm and then kept in the greenhouse until disease developed on the untreated control plants.

Leaf Blotch of Wheat (*Septoria tritici*-SEPTTR): Wheat (cultivar Monon) was grown in a soilless peat-based potting mixture ("Metromix") until the seedlings were 10–20 cm tall. These plants were then sprayed to run off with the test compound at a rate of 100 ppm. After 24 hours the test plants were inoculated by spraying with an aqueous spore suspension of *Septoria tritici*. The plants were then transferred to the greenhouse until disease developed on the untreated control plants.

Glume Blotch of Wheat (*Septoria nodorum*-LEPTNO): Wheat (cultivar Monon) was grown in a soilless peat-based potting mixture ("Metromix") until the seedlings were 10–20 cm tall. These plants were then sprayed to run off with the test compound at a rate of 100 ppm. After 24 hours the test plants were inoculated by spraying with an aqueous spore suspension of *Septoria nodorum*. The plants were then transferred to the greenhouse until disease developed on the untreated control plants.

Wood Decay Fungi—In Vitro methods: Cultures of *Gloeophyllum trabeum* and *Trametes versicolor* are grown by submerged culture in Potato Dextrose—0.5% Yeast Extract (PDY) broth for approximately 7 days prior to use. Mycelia are harvested by filtration, resuspended in fresh PDY broth, and fragmented using a sterilized stainless steel blender cup. Prior to inoculating plates inoculum suspensions are adjusted to a standard concentration determined by optical density. Test compounds are dissolved in DMSO and added to 96 well microtiter plates. Two hundred $\mu l$ of inoculum-PDY are added to each well. Percent inhibition is determined by comparing growth in treated wells after 3 to 5 days to growth observed in solvent blank wells.

The following table presents the activity of typical compounds of the present invention when evaluated in these experiments. The test compounds were used at a rate of 100 ppm. The effectiveness of the test compounds in controlling disease was rated using the scale shown in the Key on the Table.

| Compound Number | PLASVI GDM | PLASVI Curative | PHYTIN LBT | VENTIN SA | PUCCRT LRW | PYRIOR RB | CERCBE | ERYSGT PMW | SEPTTR STW | LEPTNO SNW | Gloeophyllum trabeum | Trametes versicolor |
|---|---|---|---|---|---|---|---|---|---|---|---|---|
| 501 | ++ | | | | | | | | | ++ | | |
| 502 | ++ | | | ++ | + | ++ | | - | | ++ | ++ | ++ |
| 503 | ++ | | | ++ | ++ | ++ | | ++ | | ++ | ++ | ++ |
| 504 | ++ | + | ++ | ++ | ++ | ++ | ++ | + | | ++ | | |
| 505 | ++ | - | | - | - | - | | - | - | - | | |
| 506 | ++ | - | | | | | | - | - | + | | |
| 507 | ++ | - | | | | | | - | - | + | | |
| 508 | ++ | - | | | | | | + | | | | |
| 509 | ++ | - | - | | + | | | - | - | | ++ | ++ |
| 510 | ++ | - | + | | ++ | | | - | + | | + | + |
| 511 | ++ | - | ++ | | - | | | - | - | | | |
| 512 | ++ | - | ++ | | ++ | | | - | ++ | | | |
| 513 | ++ | - | ++ | | ++ | | | - | - | | | |
| 514 | ++ | ++ | ++ | | ++ | | ++ | ++ | - | ++ | | |
| 515 | ++ | + | ++ | | ++ | | | - | ++ | | | |
| 516 | ++ | - | ++ | | ++ | | | - | - | | | |
| 517 | ++ | - | ++ | | ++ | | | - | ++ | ++ | | |
| 518 | ++ | - | ++ | | ++ | | | - | - | | | |
| 519 | ++ | - | ++ | | ++ | | | ++ | ++ | + | ++ | ++ |
| 520 | ++ | - | ++ | | ++ | | | ++ | - | | ++ | ++ |
| 521 | ++ | - | ++ | | ++ | | | - | - | | | |
| 522 | ++ | ++ | ++ | | ++ | ++ | + | - | + | ++ | | |
| 523 | ++ | ++ | ++ | | + | | ++ | - | ++ | | | |
| 524 | ++ | - | ++ | | - | | | - | - | ++ | | |
| 525 | ++ | + | | | + | | | - | ++ | | | |
| 526 | ++ | ++ | ++ | | ++ | | | - | ++ | | | |
| 527 | ++ | - | ++ | | ++ | | | - | ++ | | | |
| 528 | ++ | - | ++ | | ++ | | | - | ++ | | | |
| 529 | ++ | - | ++ | | ++ | | | - | - | | | |
| 530 | ++ | - | ++ | | ++ | | | - | ++ | ++ | ++ | ++ |
| 531 | ++ | - | ++ | | ++ | | | - | + | + | ++ | ++ |
| 532 | ++ | - | | | ++ | | | - | ++ | | ++ | ++ |
| 533 | ++ | - | | | ++ | | | - | + | | ++ | ++ |
| 534 | ++ | - | ++ | | ++ | | | - | ++ | + | | |
| 535 | ++ | - | ++ | | ++ | | | - | + | - | ++ | ++ |
| 536 | ++ | - | ++ | | ++ | | | - | + | | ++ | ++ |
| 537 | ++ | - | ++ | | ++ | | | - | - | | ++ | ++ |
| 538 | ++ | + | ++ | | ++ | | | - | ++ | | ++ | ++ |
| 539 | ++ | + | ++ | | ++ | | | - | + | | | |
| 540 | ++ | - | ++ | | ++ | | | + | + | | ++ | ++ |
| 541 | ++ | - | ++ | | ++ | | | - | ++ | | ++ | ++ |
| 542 | ++ | - | ++ | | ++ | | | - | - | | | |
| 543 | ++ | - | ++ | | ++ | | | - | ++ | | ++ | ++ |
| 544 | ++ | - | ++ | | + | | | - | + | | | |
| 545 | ++ | - | - | | - | | | - | - | - | | |
| 546 | + | - | | | ++ | | | - | - | | ++ | ++ |
| 547 | ++ | - | | | + | | | | - | | | |
| 548 | + | | | | - | | | | - | - | ++ | ++ |

-continued

| Compound Number | PLASVI GDM | PLASVI Curative | PHYTIN LBT | VENTIN SA | PUCCRT LRW | PYRIOR RB | CERCBE | ERYSGT PMW | SEPTTR STW | LEPTNO SNW | Gloeophyllum trabeum | Trametes versicolor |
|---|---|---|---|---|---|---|---|---|---|---|---|---|
| 549 | ++ | - | - |  | - |  |  | - | - |  |  |  |
| 550 | ++ | + | ++ |  | + |  |  | - | + |  |  |  |
| 551 | - | - | - |  | + |  |  | - | + |  |  |  |
| 552 | ++ | - | ++ |  | ++ |  |  | - | - |  |  |  |
| 553 | ++ | - | ++ |  | + |  |  | - | + |  |  |  |
| 554 | - | - | + |  | ++ |  |  | - | - |  |  |  |
| 555 | - | + | ++ |  | + |  |  | - | ++ |  |  |  |
| 556 | ++ | ++ | ++ |  | ++ |  |  | - | + |  |  |  |
| 557 | ++ | ++ | + |  | - |  |  | - | - |  | ++ | ++ |
| 558 | ++ | - | ++ |  | ++ |  |  | - | - |  |  |  |
| 559 | ++ | ++ | ++ |  | - |  |  | - | - |  | ++ | ++ |
| 560 | + | - | + |  | ++ |  |  | - | - |  |  |  |
| 561 | ++ | - | ++ |  | - |  |  | - | - |  |  |  |
| 562 | ++ |  | ++ |  | ++ |  |  | - | - |  |  |  |
| 563 | ++ |  | ++ |  | + |  |  | - | - |  |  |  |
| 564 | ++ |  | + |  | - |  |  | ++ | - |  |  |  |
| 565 | ++ |  | ++ |  | ++ |  |  | - | - |  |  |  |
| 566 | ++ |  | ++ |  | + |  |  | - | + |  |  |  |
| 567 | ++ |  | ++ |  | + |  |  | - | - |  |  |  |
| 568 | ++ |  | ++ |  | ++ |  |  | - | - |  |  |  |
| 569 | ++ |  | + |  | + |  |  | - | - |  |  |  |
| 570 | ++ |  | ++ |  | ++ |  |  | - | - |  |  |  |
| 571 | ++ |  | ++ |  | ++ |  |  | - | - |  |  |  |
| 572 | ++ |  | ++ |  | - |  |  | - | - |  |  |  |
| 573 | ++ |  | + |  | - |  |  | + | - |  |  |  |
| 574 | ++ |  | ++ |  | + |  |  | + | - |  |  |  |
| 575 | ++ |  | ++ |  | - |  |  | - | - |  |  |  |
| 576 | ++ |  | ++ |  | ++ |  |  | - | - |  |  |  |
| 577 | ++ |  | ++ |  | + |  |  | - | - |  |  |  |
| 578 | ++ |  | ++ |  | ++ |  |  | - | - |  |  |  |
| 579 | ++ |  | ++ |  | + |  |  | - | - |  |  |  |
| 580 | ++ |  | ++ |  | ++ |  |  | - | - |  |  |  |
| 581 | ++ |  | ++ |  | ++ |  |  | - | - |  |  |  |
| 582 | ++ |  | - |  | + |  |  | - | - |  |  |  |
| 583 | ++ |  | ++ |  | - |  |  | - | - |  |  |  |
| 584 | ++ |  | ++ |  | - |  |  | - | - |  |  |  |
| 585 | ++ |  | ++ |  | + |  |  | - | - |  |  |  |
| 586 | ++ |  | - |  | - |  |  | - | - |  |  |  |
| 587 | + |  | + |  | ++ |  |  | - | - |  |  |  |
| 588 | ++ |  | ++ |  | ++ |  |  | - | + |  |  |  |
| 589 | ++ |  | ++ |  | ++ |  |  | - | - |  |  |  |
| 590 | ++ |  | ++ |  | ++ |  |  | - | + |  |  |  |
| 591 | ++ |  | ++ |  | ++ |  |  | - | + |  |  |  |
| 592 | ++ |  | ++ |  | - |  |  | - | ++ |  |  |  |
| 593 | ++ |  | ++ |  | + |  |  | - | - |  |  |  |
| 594 | ++ |  | ++ |  | + |  |  | - | - |  |  |  |
| 595 | ++ |  | ++ |  | ++ |  |  | - | - |  |  |  |
| 596 | ++ |  | ++ |  | + |  |  | - | - |  |  |  |
| 597 | ++ |  | ++ |  | + |  |  | - | - |  |  |  |

-continued

| Compound Number | PLASVI GDM | PLASVI Curative | PHYTIN LBT | VENTIN SA | PUCCRT LRW | PYRIOR RB | CERCBE | ERYSGT PMW | SEPTTR STW | LEPTNO SNW | Gloeophyllum trabeum | Trametes versicolor |
|---|---|---|---|---|---|---|---|---|---|---|---|---|
| 598 | ++ | | | | | | | | − | | | |
| 599 | + | | | | | | | + | | | | |
| 600 | ++ | | ++ | | ++ | | | − | − | | | |
| 601 | ++ | | − | | − | | | − | − | | | |
| 602 | ++ | | ++ | | − | | | − | − | | | |
| 603 | ++ | − | ++ | | ++ | | | − | + | | | |
| 604 | ++ | − | ++ | | ++ | | | + | + | | | |
| 605 | ++ | − | ++ | | ++ | | | − | ++ | | | |
| 606 | ++ | − | ++ | | ++ | | | − | − | | | |
| 607 | + | − | − | | − | | | − | − | | | |
| 608 | ++ | − | ++ | | − | | | − | − | | | |
| 609 | + | − | + | | ++ | | | − | − | | | |
| 610 | ++ | − | ++ | | + | | | − | ++ | | | |
| 611 | ++ | − | − | | − | | | − | − | | | |
| 612 | ++ | − | ++ | | ++ | | | − | − | | | |
| 613 | ++ | − | − | | + | | | − | − | | | |
| 614 | ++ | + | ++ | | ++ | | | − | ++ | ‡‡ | + | + |
| 615 | ++ | − | ++ | | ++ | | | ‡ | − | ‡ | ‡‡ | ‡ |
| 616 | ++ | − | ++ | | ++ | | | − | + | | + | + |
| 617 | ++ | − | ++ | | ++ | | | ‡ | − | | + | + |
| 618 | ++ | − | ++ | | ++ | | | − | ++ | | ++ | ++ |
| 619 | ++ | − | ++ | | ++ | | | − | + | | + | + |
| 620 | ++ | − | ++ | | ++ | | | − | − | | ‡ | ‡ |
| 621 | ++ | − | ++ | | ++ | | | − | ‡ | | + | + |
| 622 | ++ | + | ++ | | ++ | | | − | + | | + | ++ |
| 623 | ++ | + | ++ | | ++ | | | − | − | ‡‡ | ‡‡ | ‡‡ |
| 624 | ++ | − | ++ | | ++ | | | − | ++ | | + | + |
| 625 | ++ | − | ++ | | ++ | | | − | + | ‡‡ | + | + |
| 626 | ++ | − | ++ | | + | | | − | − | | + | + |
| 627 | ++ | − | ++ | | − | | | − | + | | + | + |
| 628 | ++ | + | ++ | | ++ | | | ‡ | − | ‡‡ | ++ | ++ |
| 629 | ++ | + | ++ | | + | | | − | + | + | + | + |
| 630 | ++ | + | ++ | | ++ | | | − | − | ‡ | − | − |
| 631 | ++ | ‡ | ++ | | ++ | | | − | − | | ‡ | ‡ |
| 632 | ++ | − | ++ | | − | | | − | + | | + | + |
| 633 | ++ | − | ++ | | ++ | | | − | − | | + | + |
| 634 | ++ | − | ++ | | ++ | | | ‡ | + | ‡ | ++ | ++ |
| 635 | ++ | − | ++ | | − | | | − | + | + | ‡ | ‡ |
| 636 | ++ | − | ++ | | ++ | | | − | ‡ | | + | + |
| 637 | ++ | − | ++ | | − | | | − | − | | − | − |
| 638 | ++ | − | ++ | | ++ | | | − | − | | ‡ | ‡ |
| 639 | ++ | − | ++ | | ++ | | | − | − | | + | + |
| 640 | ++ | − | ++ | | + | | | − | − | | + | + |
| 641 | ++ | + | ++ | | ++ | | | + | − | | ‡ | ‡ |
| 642 | ++ | − | ++ | | ++ | | | − | − | | ‡ | ‡ |
| 643 | ++ | − | ++ | | ++ | | | − | − | | + | + |
| 644 | ++ | − | ++ | | + | | | − | − | | + | + |
| 645 | ++ | − | ++ | | ++ | | | − | − | | ‡ | ‡ |
| 646 | ++ | − | ++ | | − | | | − | − | | − | − |

-continued

| Compound Number | PLASVI GDM | PLASVI Curative | PHYTIN LBT | VENTIN SA | PUCCRT LRW | PYRIOR RB | CERCBE | ERYSGT PMW | SEPTTR STW | LEPTNO SNW | Gloeophyllum trabeum | Trametes versicolor |
|---|---|---|---|---|---|---|---|---|---|---|---|---|
| 647 | ++ | - | ++ | | | | | - | + | | | ++ |
| 648 | ++ | | ++ | | ++ | | | | | ++ | + | ++ |
| 649 | ++ | + | + | | | | | | ++ | | ++ | ++ |
| 650 | ++ | - | ++ | | | | | | + | + | | |
| 651 | ++ | - | ++ | | ++ | | | - | ++ | ++ | | |
| 652 | ++ | - | ++ | | ++ | | | - | + | + | | |
| 653 | ++ | ++ | ++ | | ++ | | | - | - | ++ | | |
| 654 | ++ | - | ++ | | ++ | | | - | + | + | + | ++ |
| 655 | ++ | ++ | ++ | | + | | | - | + | ++ | | |
| 656 | ++ | - | ++ | | ++ | | | - | ++ | - | | |
| 657 | ++ | - | + | | - | | | - | - | ++ | | |
| 658 | ++ | - | ++ | | - | | | - | - | - | | |
| 659 | ++ | - | ++ | | + | | | - | - | ++ | | |
| 660 | ++ | - | ++ | | ++ | | | - | - | - | | |
| 661 | ++ | - | ++ | | ++ | | | - | ++ | ++ | | |
| 662 | ++ | - | ++ | | ++ | | | - | ++ | ++ | | |
| 663 | ++ | ++ | ++ | | ++ | | | - | ++ | ++ | | |
| 664 | ++ | - | ++ | | ++ | | | - | ++ | ++ | | |
| 665 | ++ | ++ | ++ | | ++ | | | - | ++ | - | | |
| 666 | ++ | - | ++ | | ++ | | | - | ++ | ++ | | |
| 667 | ++ | + | ++ | | + | | | - | - | ++ | | |
| 668 | ++ | - | - | | ++ | | | - | ++ | - | | |
| 669 | ++ | - | ++ | | + | | | - | ++ | ++ | | |
| 670 | ++ | - | ++ | | - | | | - | - | - | | |
| 671 | ++ | - | ++ | | - | | | - | - | + | | |
| 672 | ++ | - | ++ | | - | | | - | - | ++ | | |
| 673 | - | - | ++ | | ++ | | | - | - | - | | |
| 674 | ++ | - | ++ | | - | | | - | - | - | | |
| 675 | ++ | - | ++ | | - | | | - | - | - | | |
| 676 | ++ | - | ++ | | - | | | - | - | - | | |
| 677 | ++ | - | ++ | | + | | | - | - | - | | |
| 678 | ++ | - | ++ | | - | | | | | | | |
| 679 | | | | | | | | | | ++ | | |
| 680 | | | | | | | | | | | | |

Key:
blank space = not tested
- = 0–29% control of plant disease
+ = 30–74% control of plant disease
++ = 75–100% control of plant disease
rate = 100 ppm unless specified otherwise in biology method While the invention has been illustrated and described in detail in the foregoing description, the same is to be considered illustrative and not restrictive in character, it being understood that only the preferred embodiment has been described and that all changes and modifications that come within the spirit of the invention are desired to be protected.

What is claimed is:

1. A 3-nitrosalicylamide of the formula

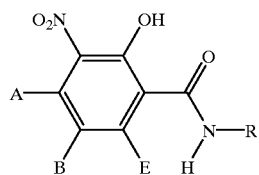

wherein

A is selected from the group consisting of H or F,

B is selected from the group consisting of H, F, or Cl,

E is selected from the group consisting of H, OH, or F, and

R is

R is 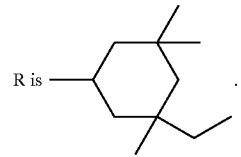

* * * * *